United States Patent
Forsell

(10) Patent No.: US 11,337,791 B2
(45) Date of Patent: *May 24, 2022

(54) ARTIFICIAL STOMACH

(71) Applicant: Peter Forsell, Bouveret (CH)

(72) Inventor: Peter Forsell, Bouveret (CH)

( * ) Notice: Subject to any disclaimer, the term of this patent is extended or adjusted under 35 U.S.C. 154(b) by 219 days.

This patent is subject to a terminal disclaimer.

(21) Appl. No.: 16/665,160

(22) Filed: Oct. 28, 2019

(65) Prior Publication Data

US 2020/0163748 A1 May 28, 2020

Related U.S. Application Data

(63) Continuation of application No. 15/513,433, filed on Jun. 5, 2017, now Pat. No. 10,456,238, which is a continuation of application No. 14/074,963, filed on Nov. 8, 2013, now Pat. No. 9,668,851, which is a continuation of application No. 13/122,809, filed as application No. PCT/SE2009/051158 on Oct. 12, 2009, now Pat. No. 8,579,987.

(60) Provisional application No. 61/227,815, filed on Jul. 23, 2009.

(51) Int. Cl.
| | |
|---|---|
| *A61F 2/04* | (2013.01) |
| *A61B 5/0205* | (2006.01) |
| *A61B 5/07* | (2006.01) |
| *A61B 5/11* | (2006.01) |
| *A61F 5/00* | (2006.01) |

(52) U.S. Cl.
CPC ............ *A61F 2/04* (2013.01); *A61B 5/02055* (2013.01); *A61B 5/076* (2013.01); *A61B 5/1107* (2013.01); *A61F 5/0013* (2013.01); *A61F 2002/045* (2013.01); *A61F 2250/0001* (2013.01); *A61F 2250/0004* (2013.01)

(58) Field of Classification Search
CPC . A61F 2/04; A61F 2002/45; A61F 2250/0001
USPC .............................................. 623/23.65–23.7
See application file for complete search history.

(56) References Cited

U.S. PATENT DOCUMENTS

| | | | | |
|---|---|---|---|---|
| 3,950,406 | A * | 4/1976 | Floyd, Jr. ............. | C07C 405/00 562/503 |
| 5,370,134 | A * | 12/1994 | Chin ................ | A61B 17/00234 128/898 |
| 8,579,987 | B2 * | 11/2013 | Forsell ...................... | A61F 2/04 623/23.65 |
| 8,696,761 | B2 * | 4/2014 | Forsell ...................... | A61F 2/04 623/23.65 |
| 9,668,851 | B2 * | 6/2017 | Forsell ...................... | A61F 2/04 |
| 9,763,768 | B2 * | 9/2017 | Forsell ...................... | A61F 2/04 |
| 10,456,238 | B2 * | 10/2019 | Forsell ...................... | A61F 2/04 |
| 10,835,363 | B2 * | 11/2020 | Forsell ...................... | A61F 2/04 |
| 2007/0265709 | A1 * | 11/2007 | Rajan ...................... | A61F 5/003 623/23.64 |
| 2009/0287045 | A1 * | 11/2009 | Mitelberg .......... | A61B 1/00135 600/104 |

(Continued)

*Primary Examiner* — Suzette J Gherbi

(57) ABSTRACT

"An artificial stomach for replacing the normal stomach of a patient comprises a food reservoir adapted to collect food, an inlet connected to a first opening of the food reservoir and further being adapted to upstream connect to the patient's gastrointestinal tract, and an outlet connected to a second opening of the food reservoir and further being adapted to downstream connect to the patient's gastrointestinal tract".

22 Claims, 19 Drawing Sheets

(56) References Cited

U.S. PATENT DOCUMENTS

| | | | |
|---|---|---|---|
| 2010/0081883 A1* | 4/2010 | Murray | A61B 17/3423 600/204 |
| 2010/0210999 A1* | 8/2010 | Laufer | A61B 17/22031 604/28 |
| 2011/0196506 A1* | 8/2011 | Forsell | A61F 2/04 623/23.65 |
| 2012/0277742 A1* | 11/2012 | Laufer | A61B 18/14 606/45 |
| 2013/0331854 A1* | 12/2013 | Saldinger | A61B 17/50 606/113 |
| 2014/0303746 A1* | 10/2014 | Forsell | A61F 2/04 623/23.65 |

* cited by examiner

ARTIFICIAL STOMACH

This application is a continuation of U.S. application Ser. No. 15/613,433, filed 2017, Jun. 05, which is a continuation of U.S. application Ser. No. 14/074,963, filed 2013, Nov. 08, now U.S. Pat. No. 9,668,851, which is a continuation of U.S. application Ser. No. 13/122,809, filed 2011, Apr. 06, now U.S. Pat. No. 8,579,987, which is the U.S national phase of International Application No. PCT/SE2009/051158, filed on 2009, Oct. 12, and which claims the benefit of U.S Provisional Application No. 61/227,815, filed on 2009, Jul. 23, and which claims priority from Swedish National application 0802160-2 filed on 2008, Oct. 10.

FIELD OF INVENTION

The present invention generally relates to implantation and more particularly to an artificial stomach implantable into a human or animal patient. The invention also relates to methods of placing and using an artificial stomach.

BACKGROUND

Stomach cancer is a serious condition and to save life it has been shown that the whole stomach needs to be surgically removed although the cancer may be small. Patients with stomach cancer normally get their whole stomach surgically removed, the operation called total gastrectomy. This means the oesophagus and the intestine is sutured together. These patients quality of life is dramatically reduced. Their food supply is normally without both reservoir and valves-creating serious problems in terms of ability to eat and ability to keep the weight.

The placement of the normal stomach 102 of a person 100 is seen in FIG. 1. A more detailed view of the anatomy of a normal stomach is shown in FIG. 2a. In the gastrointestinal tract, the oesophagus 202 normally transcends into the stomach 204 at the cardia area 206. The stomach 204 then transcends downstream into the duodenum 212 of the intestine 210 at the pyloris 208. For persons having their stomach 204 surgically removed (hereinafter referred to as patients), one method is to surgically connect the oesophagus 202 directly to the intestine 210. The result of such a surgical operation is shown in FIG. 2b. The most proximal part of the intestine 210, i.e. the duodenum 212, is not able to reach to the oesophagus 202 and therefore the proximal jejunum 214 is cut and the distal side sutured to the oesophagus 202 and the proximal part of the jejunum 214 comprising duodenum 212 and the gall connection proximal is sutured end to side to jejunum 214 further distal creating a so called Roux-en-Y-connection.

Because it is not easy to reach the oesophagus 202 with the intestine 210, they are normally connected end to end like a tube without any reservoir or valves. Normally the cardia 206 (the ring muscle between the stomach and oesophagus) keeps the food passage way closed to avoid reflux problems but cardia 206 is normally removed when performing a Roux-en-Y operation.

The overall result is a very unpleasant situation for the patient. The patients have large difficulties to keep their weight and normally feel themselves in a really bad shape, with several food related bad feelings. The situation for the patients is so complicated that studies have shown a dramatic increase in suicide in this group of patients.

Furthermore, there exist also other possible solutions, such as xenotransplantations and intravenous drip. Xenotransplantation is a method where an organ from an animal is transplanted to a patient. However, the immune rejection effects are serious and the method is not a usable alternative. The method of living with a nutrition drip has various disadvantages, for instance the patient needs to bring droplet equipment and loses also the moment of eating. The situation of life for a patient with nutrition drip is far from natural.

The ability to replace the stomach with an artificial stomach would increase quality of life dramatically for these patients. Such an artificial stomach may be used independently of the reason for removing the stomach.

SUMMARY OF THE INVENTION

An object of the present invention is to provide a solution to the above described problem for patients which have had their stomach surgically removed.

The invention is based on the realisation that an implanted artificial stomach can replace a natural stomach, which has been removed.

Thus, according to one embodiment of the invention there is provided an artificial stomach for replacing the normal stomach of a patient, comprising: a food reservoir adapted to collect food, an inlet connected to a first opening of the food reservoir and further being adapted to upstream connect to the patient's gastrointestinal tract, and an outlet connected to a second opening of the food reservoir and further being adapted to downstream connect to the patient's gastrointestinal tract.

In the preferred embodiment:

An artificial stomach for replacing the normal stomach of a patient, comprising:

a food reservoir adapted to collect food, an inlet connected to a first opening of the food reservoir and further being adapted to upstream connect to the patient's gastrointestinal tract, and an outlet connected to a second opening of the food reservoir and further being adapted to downstream connect to the patient's gastrointestinal tract, wherein an outer wall encloses both the food reservoir and a servo reservoir for regulating the size of the food reservoir, the food reservoir and the servo reservoir being separated by a flexible inner wall, where further both the food reservoir wall and the wall of the servo reservoir comprise parts of the outer wall and the flexible inner wall.

Preferable the artificial stomach comprises an inlet valve connected between the patient's gastrointestinal tract and the first opening of the food reservoir The artificial stomach may be implantable in the patient's abdomen and may have the inlet further adapted to upstream connect to the oesophagus. The inlet may also be further adapted to upstream connect to the intestine.

In one embodiment the inlet valve is connected between the inlet and the first opening of the food reservoir or the artificial stomach comprises an inlet valve unit comprising an inlet valve connected between the patient's gastrointestinal tract and the first opening of the food reservoir.

The inlet valve is preferable adapted to open correlated to when food in the gastrointestinal tract upstream is transported down. Alternatively the inlet valve is adapted to open correlated to when a contracting wave is propagating along the gastrointestinal tract upstream or adapted to open correlated to when food is reaching the inlet valve.

In another embodiment the inlet valve unit comprising at least one connector adapted to upstream connect the inlet to the patient's gastrointestinal tract. The connector may comprise a sleeve adapted to cover a part of the wall of the gastrointestinal tract, wherein the sleeve preferable has a structure adapted to promote in-growth of human tissue into the sleeve.

The artificial stomach preferable the inlet valve unit may further comprising a burp output, wherein the burp output further comprises a burp valve connecting the food reservoir with the inlet valve proximal to said burp valve.

The artificial stomach preferable have an outer wall that encloses both the food reservoir and a servo reservoir for regulating the size of the food reservoir, the food reservoir and the servo reservoir being separated by a flexible inner wall, where further both the food reservoir wall and the wall of the servo reservoir comprise parts of the outer wall and the flexible inner wall, wherein said servo reservoir is adapted to be filled with fluid in small steps, wherein the food reservoir is adapted to be emptied by the servo reservoir in small steps, when said servo reservoir is filled with said fluid in small steps, thereby emptying food in small steps into the intestine, when said artificial stomach is implanted.

The food reservoir is normally adapted to empty step by step, small portions of food at a time.

In yet another embodiment the artificial stomach have an the outlet valve adapted to functioning passively and opens related to a volume decrease in the food reservoir.

The artificial stomach normally include a servo reservoir, adapted to have a variable size and to be filled with different amounts of fluid. The servo reservoir in this embodiment is adapted to have a shape allowing variation in size without limitation from surrounded fibrosis, covering the implant when implanted.

The artificial stomach further may include a hydraulic fluid reservoir, hydraulically connected to said servo reservoir and a pump for fluid connecting the fluid supply reservoir to the servo reservoir. Preferable said pump is adapted to reversible move fluid between the servo reservoir and the hydraulic fluid reservoir.

In the artificial stomach according to another embodiment, an outer wall encloses both the food reservoir and a servo reservoir for regulating the size of the food reservoir, the food reservoir and the servo reservoir being separated by a flexible inner wall, where further both the food reservoir wall and the wall of the servo reservoir comprise parts of the outer wall and the flexible inner wall.

The servo reservoir may comprise a bellow.

The artificial stomach may in another embodiment have said servo reservoir adapted to be regulated by manually pressing a pumping reservoir in fluid connection with the servo reservoir, and may further comprising a reversed servo, wherein a small volume in the pumping reservoir is adapted to be moved manually to the servo reservoir in a closed system, compressed with a higher force per area unit and wherein said servo reservoir is adapted to create a larger volume change in a second closed system, having less force per area unit.

Preferable the artificial stomach having the outer wall being rigid. In one embodiment the stomach food part comprises the food reservoir and the servo reservoir, and where the hydraulic fluid reservoir is separated from the stomach food part by the rigid outer wall and is further enclosed by a fluid reservoir wall, In yet another embodiment the food reservoir is adapted to increase in volume when filled with food when the patient is eating, thereby causing a reduction in the volume of the servo reservoir, in turn moving fluid from said servo reservoir to said hydraulic fluid reservoir.

The artificial stomach outlet is further normally adapted to downstream connect to the intestine.

The artificial stomach preferable comprising an outlet valve connected between the second opening of the food reservoir and the outlet, wherein the outlet valve is adapted to open when the food reservoir should be emptied. Alternatively the outlet valve is adapted to open at a regulated rate.

In the artificial stomach according to another embodiment, the food reservoir, the inlet, and the outlet are manufactured of a biocompatible material.

The artificial stomach preferably comprises at least one connector adapted to upstream connect the inlet to the patient's gastrointestinal tract, or downstream connect the outlet to the patient's gastrointestinal tract, wherein the connector preferable comprises a sleeve adapted to cover a part of the wall of the gastrointestinal tract, and wherein the sleeve preferable has a structure adapted to promote in-growth of human tissue into the sleeve.

Thus the artificial stomach preferably comprises a connector connecting the intestine to the outlet connector and/or a connector connecting the oesophagus or intestine to the inlet connector.

In one embodiment the artificial stomach comprising a food handling system, which may be adapted to;
mechanically handling food in the food reservoir.
moving the food around in the food reservoir.
cut the food in the food reservoir, preferable comprising electrically driven rotating knifes adapted to cut the food in the food reservoir.
squeeze the food in the food reservoir.
chemically handling food in the food reservoir.
release at least one liquid in the food reservoir, the liquid being adapted to treat the food in the food reservoir.

The liquid may comprises at least one of; an acid, an enzyme, an anti-bacterial substance.

In yet another embodiment the artificial stomach comprising a cleaning system adapted to clean the surface of the food reservoir by releasing at least one liquid into the food reservoir.

The liquid may comprises a cleaning substance and/or an anti-bacterial substance.

The artificial stomach may further comprising a special container, wherein the special container preferable is adapted to accumulate and distribute at least one liquid to the food handling system and/or, wherein the special container is adapted to accumulate and distribute at least one liquid to the cleaning system.

The artificial stomach or the system connected thereto may include a food sensor arranged outside of the food reservoir on the inlet side of the same in order to register when food is to arrive to the artificial stomach, wherein preferable the food sensor is arranged at the oesophagus wall.

The system in one embodiment include, the registration that food is to arrive to the artificial stomach is made by registering change in volume of the oesophagus or change of the curvature or elongation of the oesophagus wall.

In yet another embodiment the artificial stomach, comprising at least one connector adapted to be connected to the oesophagus or the intestine of a patient, the connector comprising a conduit fixedly attached at a first, proximal end on the outside the artificial stomach and in fluid connection to the food passageway, where the proximal part of the conduit is formed like a tube, and distal to the tube a bulge is formed.

Preferable a blocking ring is arranged to be pushed against the bulge, the ring having an inner diameter less than the outer diameter of said bulge but large enough to allow the intestinal/oesophageal wall to be placed between said ring and said tube, thereby adapted to stop said intestinal/ oesophageal wall from slipping away from the tube.

Preferable is included a flexible sleeve arranged to be rolled upon itself and then unrolled to cover part of the tube and the oesophagus or intestine, which is arranged to be pulled over the second end of the conduit sufficiently far so as to extend also over the bulge.

In one embodiment of the artificial stomach a blocking ring is arranged to be pushed over the flexible sleeve against the bulge, the ring having an inner diameter less than the outer diameter of said bulge but large enough to allow the intestinal/oesophageal wall to be placed between said ring and said tube, thereby adapted to stop said intestinal/oesophageal wall from slipping away from the tube.

The artificial stomach in one embodiment includes a return conduit arranged between the fluid reservoir and the servo reservoir for moving fluid between said servo reservoir and said hydraulic fluid reservoir via said return conduit.

In one embodiment of the artificial stomach; moving of fluid from the servo reservoir to the hydraulic fluid reservoir is done by that the food entering the food reservoir from the inlet presses on the flexible wall of the servo reservoir thus emptying fluid from there to the hydraulic fluid reservoir via a return conduit.

In another embodiment of the artificial stomach; moving of fluid from the servo reservoir to the hydraulic fluid reservoir is done by that a food sensor sends signals to the pump when food is to enters the food reservoir, the pump thus pumping out to said food corresponding amount of fluid from the servo reservoir to the hydraulic fluid reservoir.

In yet another embodiment the emptying of the food reservoir is direct or indirect regulated by a gear construction. Preferable the gear construction is driven by a motor.

The artificial stomach according to another embodiment, comprises a servo system connected to said motor, to save force against longer stroke.

Preferable a servo system is connected to said motor and a drive shaft connected to said servo system, wherein the drive shaft preferable direct or indirect affects the emptying of said food reservoir.

In another embodiment the drive shaft comprises two ends comprising a thread, spiral ridges turning in different directions at the two ends, further comprising a nut placed on the shaft at each end of the drive shaft, the food reservoir comprising two movable walls of said reservoir, wherein said nuts is adapted to be placed onto said moving walls, the motor adapted to change the volume of said food reservoir, when turning said drive shaft placed into said nuts, by moving said movable walls.

The artificial stomach may comprise an elastic material, a bio-compatible material and/or silicone.

Suitably, is provided at least one layer. For example, a metal layer, a Parylene layer, a polytetrafluoroethylene layer or a polyurethane layer. Suitably, one of the layers may be made of metal, silicon or PTFE. The layers may comprise multiple layers in any order. The volume filling device may comprise an outer surface layer of silicone, polyurethane, Teflon®, or polytetrafluoroethylene, metal, parylene, PTFE or a combination thereof. The volume filling device may comprise an inner surface layer of silicone, polyurethane, Teflon®, or polytetrafluoroethylene, metal, parylene, PTFE or a combination thereof. Other combinations of layers include but not limited to an inner surface layer of polytetrafluoroethylene and an outer layer of silicone, an inner surface layer of polytetrafluoroethylene, an intermediate layer of silicone, and an outer layer of Parylene, an inner surface layer of polyurethane and an outer layer of silicone, and an inner surface layer of polyurethane, an intermediate layer of silicone, and an outer layer of Parylene.

The fluid may comprises large molecules, such as iodine molecules, to prevent diffusion.

The system may include a fastening device for the artificial stomach comprising a first unit adapted to be implanted at a first side of the abdominal wall in the patient, and where a second unit is adapted to be implanted in the abdominal cavity of the patient at a second side of the abdominal wall, and where the artificial stomach is fastened to the fastening device, wherein preferable the first or second unit has a circular or elliptical cross-sectional shape when viewed from outside the patient's body.

In one embodiment the first and second units are covered by a cover made of material providing protection, wherein preferable the cover seals the fastening device which also may be a control assembly, thereby protecting possible electronics and other sensitive components of the control assembly.

The system may include an interconnecting device constitutes a mechanical interconnection between the first and second units so that the fastening device is kept in place by the body tissue.

In another embodiment the interconnecting device is hollow so as to house various wires, hoses etc. electrically or hydraulically interconnecting the first and second units.

According to one embodiment the device is a part of a system that may comprise a switch for manually and non-invasively controlling the device. The switch is according to one embodiment an electric switch and designed for subcutaneous implantation.

According to another embodiment the system further comprises a hydraulic device having a hydraulic reservoir, which is hydraulically connected to the device. The device could be manually regulated by pressing the hydraulic reservoir or automatically operated using a wireless remote control.

The wireless remote control system comprises, according to one embodiment, at least one external signal transmitter and an internal signal receiver implantable in the patient for receiving signals transmitted by the external signal transmitter. The system could operate using a frequency, amplitude, or phase modulated signal or a combination thereof.

According to one embodiment the wireless control signal comprises an analogue or a digital signal, or a combination of an analogue and digital signal. It is also conceivable that the signal comprises an electric or magnetic field, or a combined electric and magnetic field. According to another embodiment the wireless remote control further transmits a carrier signal for carrying the wireless control signal, said signal could comprise a digital, analogue or a combination of digital and analogue signals.

For supplying the system with energy it comprises, according to one embodiment, a wireless energy-transmission device for non-invasively energizing said device. According to said embodiment the energy-transmission device transmits energy by at least one wireless energy signal, which for example comprises a wave signal such as an ultrasound wave signal, an electromagnetic wave signal, an infrared light signal, a visible light signal, an ultra violet light signal, a laser light signal, a micro wave signal, a radio wave signal, an x-ray radiation signal and a gamma radiation signal.

It is further conceivable that the energy signal comprises an electric or magnetic field, or a combined electric and magnetic field, which can be transmitted using a carrier signal such as a digital, analogue or a combination of digital and analogue signals.

According to one embodiment the system further comprises an energy source for powering said device, which can be an implantable or external energy source or a combination thereof, in which case the internal and external energy sources can be in electric communication.

In an embodiment in which the system comprises an internal energy source, a sensor sensing a functional parameter correlated to the transfer of energy for charging the internal energy source may be provided, it is furthermore conceivable that a feedback device for sending feedback information from the inside to the outside of the patient's is provided.

According to another embodiment the system further comprises a sensor sensing a parameter such as a functional or physical parameter. Said functional parameter is, according to one embodiment, correlated to the transfer of energy for charging an internal energy source implantable in the patient. Said embodiment could furthermore comprise a feedback device for sending feedback information from inside to the outside of the patient's body and an implantable internal control unit for controlling the sensing. Above mentioned physical parameter could be one of body temperature, blood pressure, blood flow, heartbeats and breathing, and the sensor could be a pressure or motility sensor.

According to one embodiment the system could further comprise an external data communicator and an implantable internal data communicator communicating with the external data communicator, wherein the internal communicator feeds data related to said device or the patient to the external data communicator and/or the external data communicator feeds data to the internal data communicator. It is also conceivable that the system further comprises an operation device for operating said device, such as a motor or a pump, which can be electrically, hydraulically or pneumatically operated.

According to another embodiment the system has an energy-transmission device for transmitting wireless energy, wherein the wireless energy is used to directly power the operation device through for example creating kinetic energy for the operation of said device.

In embodiments where the system comprises an energy-transmission device for transmitting wireless energy, an energy-transforming device for transforming the wireless energy from a first form into a second form may be provided. Said energy-transforming device may directly power by the second form of energy. The energy could be in the form of a direct current or pulsating direct current, or a combination of a direct current and pulsating direct current, or an alternating current or a combination of a direct and alternating current, it is also conceivable that the energy is in the form of magnetic energy, kinetic energy, sound energy, chemical energy, radiant energy, electromagnetic energy, photo energy, nuclear energy or thermal energy. The system may further comprise an implantable accumulator for storing energy.

To prevent damage of the system it is conceivable that it comprises implantable electrical components including at least one voltage level guard and/or at least one constant current guard.

In a preferred embodiment, the system comprises at least one switch implantable in the patient for manually and non-invasively controlling the apparatus In another preferred embodiment, the system comprises a wireless remote control for non-invasively controlling the apparatus.

In a preferred embodiment, the system comprises a hydraulic operation device for operating the apparatus.

In one embodiment, the system comprises comprising a motor or a pump for operating the apparatus.

The method of filling the servo reservoir with fluid step by step in small steps so that the food reservoir is emptied or at least essentially emptied in small steps which results in food is received by the intestine in small subsequent portions.

Further preferred embodiments are defined by the dependent claims.

Please note that all the embodiments or features of an embodiment as well as any method or step of a method could be combined in any way if such combination is not clearly contradictory. Please also note that the description in general should be seen as describing both an apparatus or device adapted to perform a method as well as this method in itself.

BRIEF DESCRIPTION OF DRAWINGS

The invention is now described, by way of example, with reference to the accompanying drawings, in which.

DETAILED DESCRIPTION OF PREFERRED EMBODIMENTS

Briefly described, the present invention provides a solution for enabling a more natural digestive process for patients which have their natural stomach removed, by providing and implanting an artificial stomach into the patient's body.

The term "food" used in this description will hereinafter represent food or liquid, as well as any combination of food and liquid eaten or drunk by a patient. With "patient" means any human or animal, suitable to have its normal stomach replaced by an artificial stomach. The "oesophagus" is also found to be spelled esophagus. Correspondingly, oesophageal may also be spelled esophageal.

Figure 1:
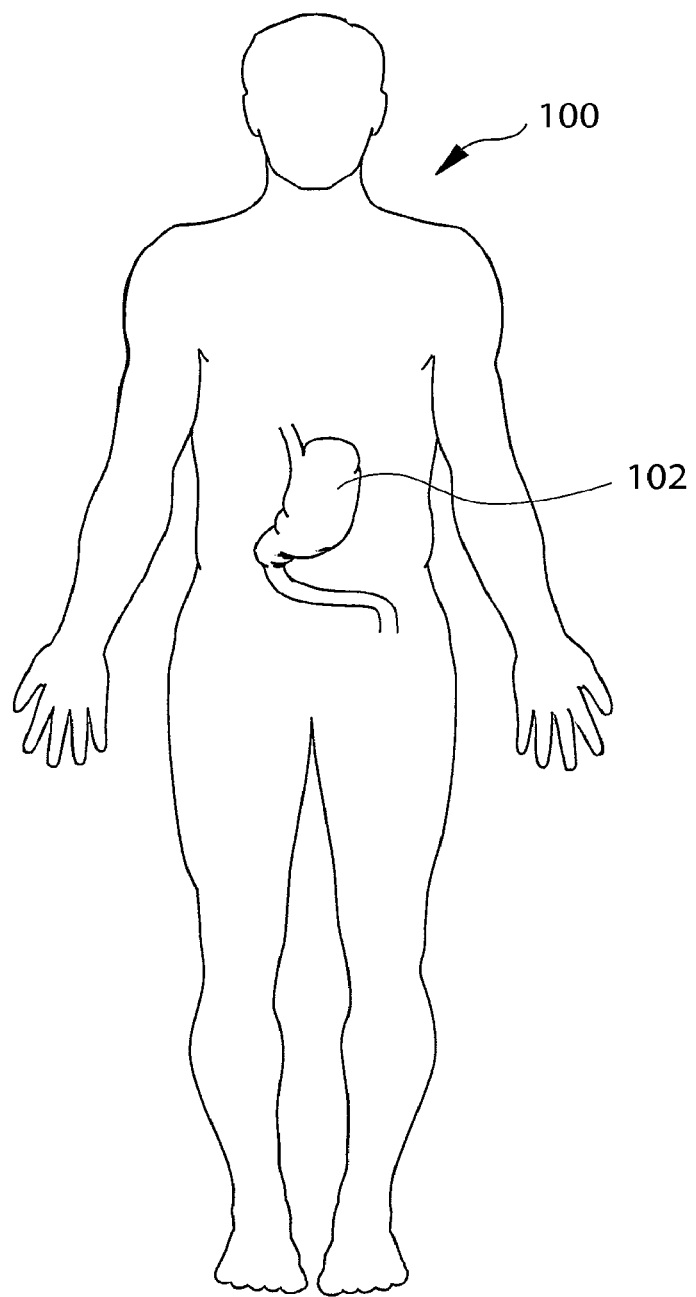
FIG. 1 is a schematic drawing illustrating a normal stomach in vivo in a person.
Figure 2A:
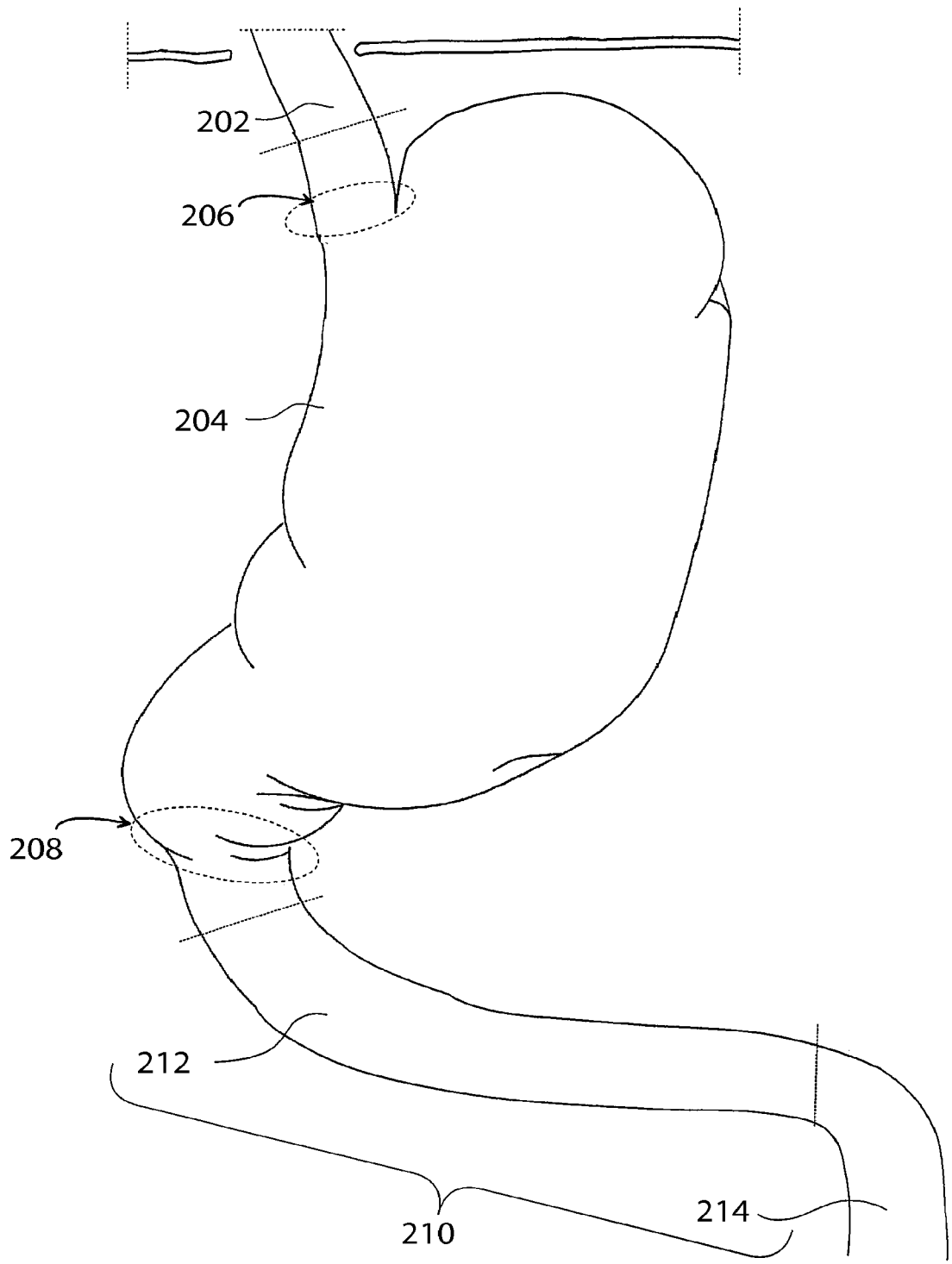
FIG. 2a is a more detailed drawing illustrating the normal stomach in vivo in a person.
Figure 2B:
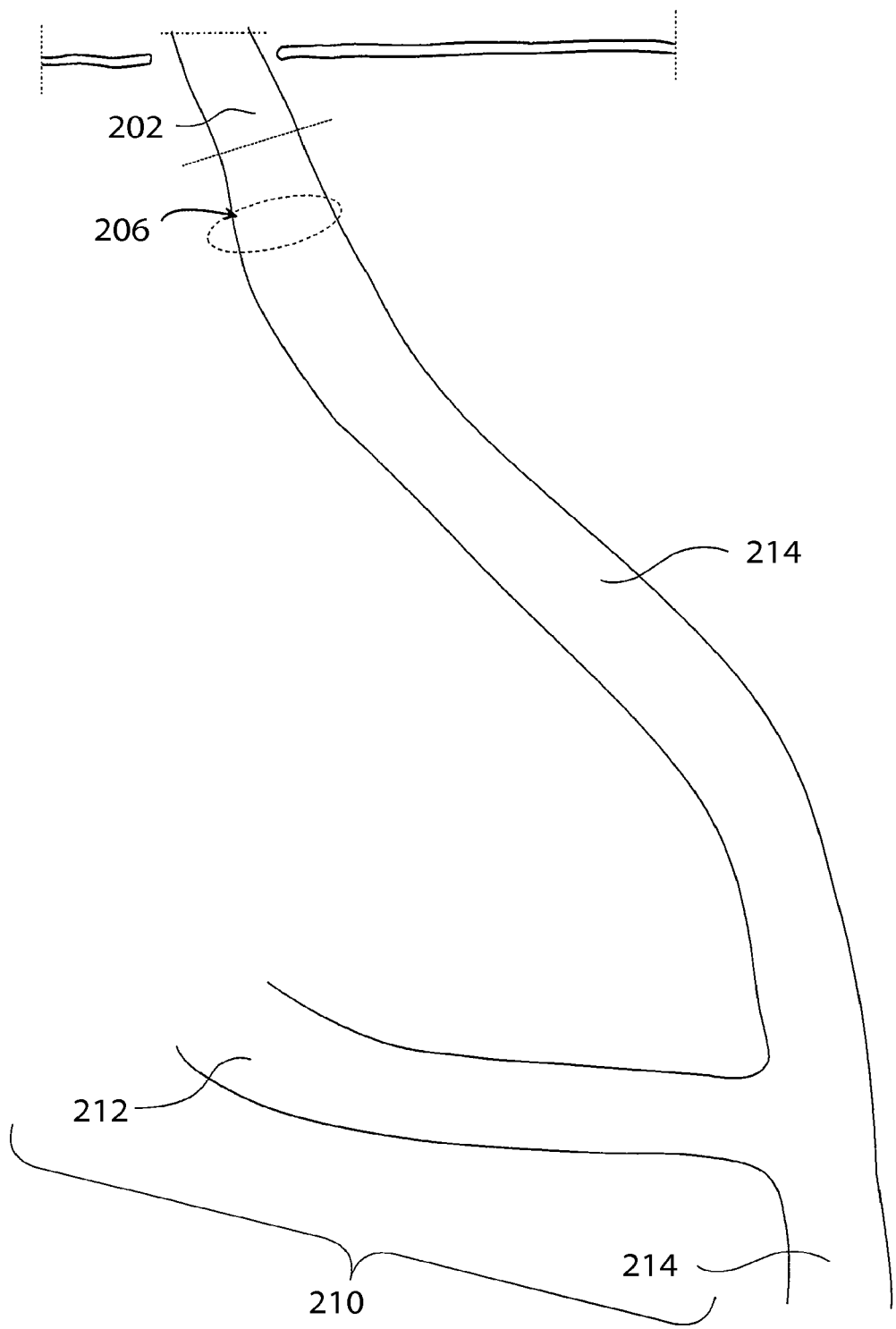
FIG. 2b is a schematic drawing illustrating the digestive system for a patient, having its normal stomach removed with the prior art Roux-en-Y method.

Prior art has been described above with reference to FIGS. 1, 2a, and 2b.

Figure 3:
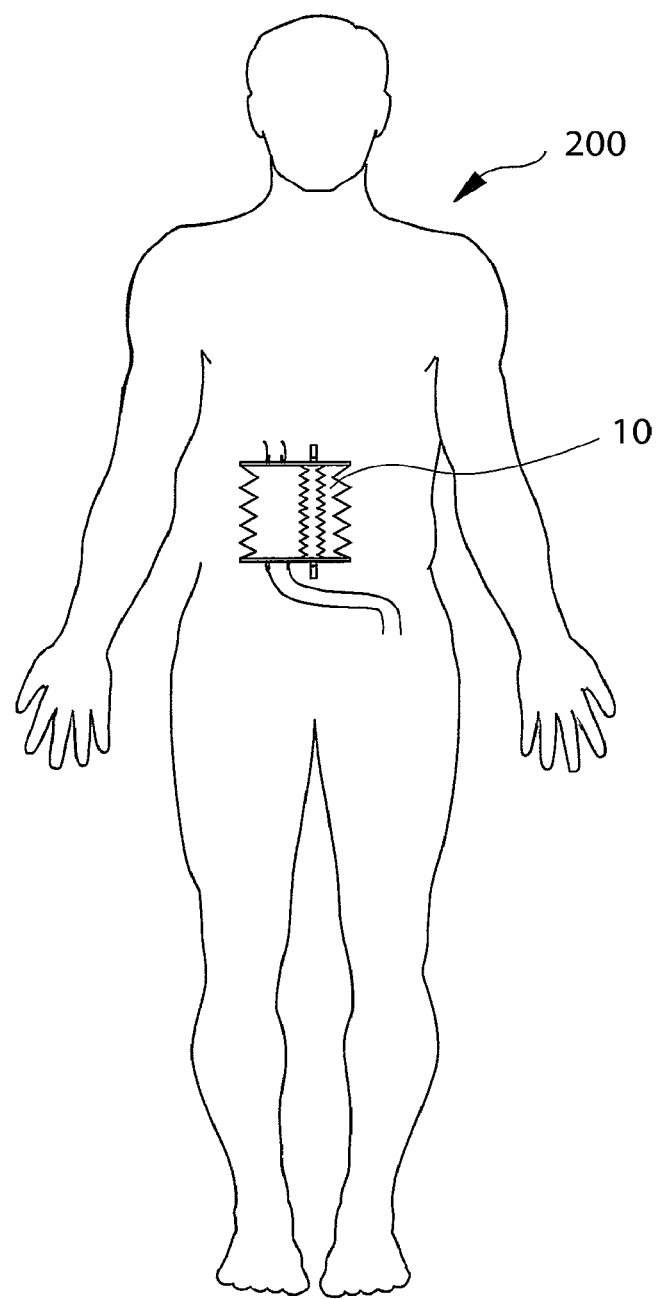
FIG. 3 is a schematic drawing illustrating an artificial stomach according to the invention in vivo in a patient.

A patient having an implanted artificial stomach in accordance with one embodiment of the present invention will now be described, with reference to FIG. 3. The artificial stomach 10 is implanted in the body of the patient 200, preferably at the same place as the normal stomach was removed from. The artificial stomach 10 may in this example be controlled by any suitable means, such as a remote control (not shown), which is either placed outside the patient's body or is implanted in the body.

Figure 4A:
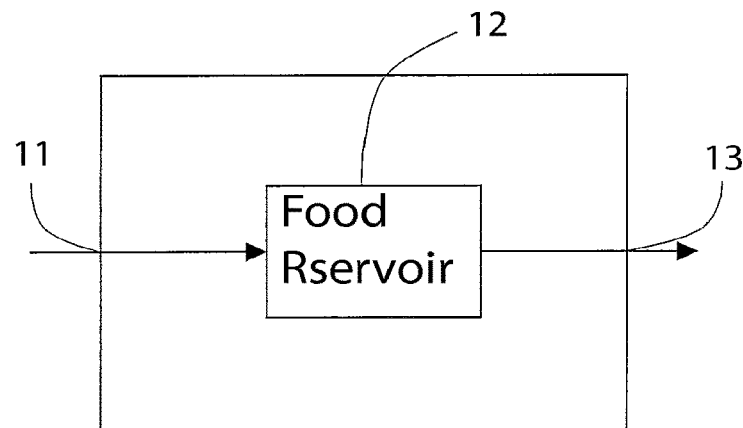
FIG. 4a is a block diagram illustrating an artificial stomach, in accordance with one embodiment.

An artificial stomach in accordance with an exemplary embodiment of the present invention will now be described with reference to FIG. 4a illustrating a block diagram. The artificial stomach 10 comprises an inlet 11, connected to a first opening of a food reservoir 12, and an outlet 13 connected to a second opening of the food reservoir 12. The inlet 11 is connected upstream to the oesophagus of a patient, and receives food when the patient eats or drinks The inlet 11 feeds the food to the food reservoir 12 that collects the food. The outlet 13 is connected downstream to the intestine of the patient, and outputs the collected food. Alternatively, the inlet 11 may instead be connected to the intestine, at a point upstream from the point the outlet 13 is connected to. This is useful for patients having their normal stomach removed and their oesophagus connected to their intestine. Preferably, the artificial stomach 10 may be adapted to be implanted in the abdomen of the patient, but may also be designed to be used on other areas inside or outside the patient's body.

Figure 7A:
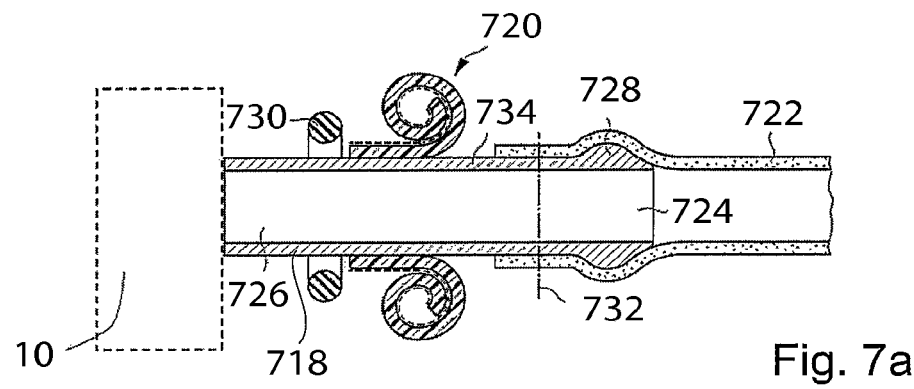
FIG. 7a is a first schematic view illustrating a connector of an artificial stomach in accordance with another embodiment.
Figure 7B:
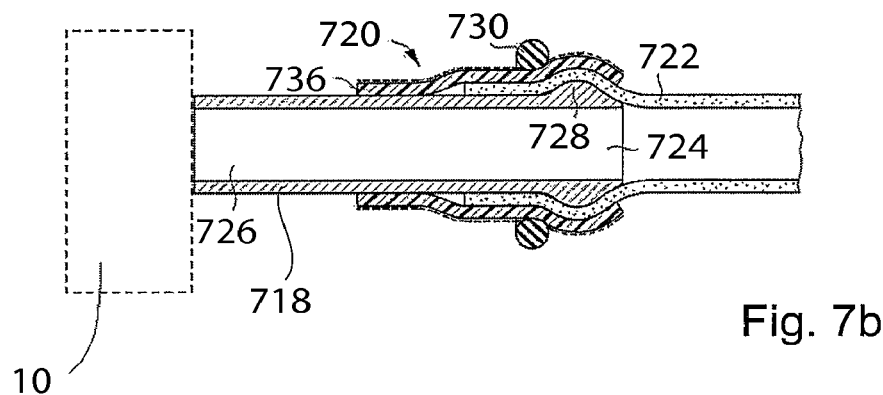
FIG. 7b is a second schematic view illustrating a connector of an artificial stomach in accordance with another embodiment.
Figure 33:
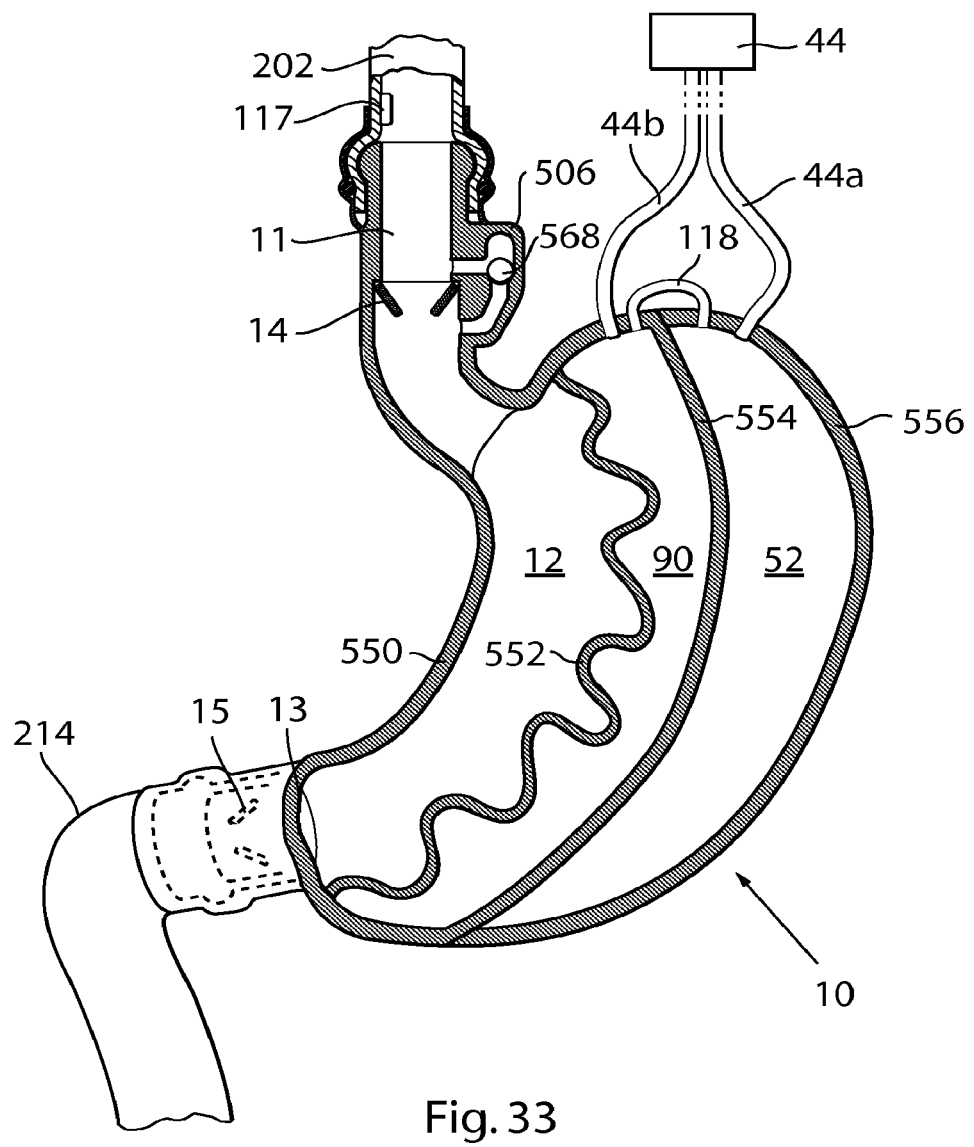
FIG. 33 is a drawing illustrating a hydraulically operated artificial stomach according to a further embodiment.

Another embodiment, different from the embodiment described above, will now be described with reference to FIG. 4b. The artificial stomach according to this embodiment comprises the corresponding inlet 11, food reservoir 12, and outlet 13, as described above, but comprises also various additional components. The artificial stomach 10 comprises an inlet valve 14 and an optional outlet valve 15, the valves opening and closing the food reservoir 12. The inlet valve 14 is adapted to open correlated to when food and/or a contracting wave in the oesophagus is transported longitudinally down the oesophagus. Optionally, the inlet valve 14 may instead be adapted to open correlated to when food and/or a contracting wave in the oesophagus is reaching the inlet valve 14. The outlet valve 15 is adapted to empty the food reservoir 12 relatively slowly into the intestine, and the outlet valve may be adapted to either open stepwise or steplessly. To connect the artificial stomach 10 to the oesophagus or intestine, an inlet connector 17 and an outlet connector 18 may be used. Such connectors, which will be described in detail below with reference to FIGS. 7a and 7b, are described in the provisional U.S. patent applications Nos. 60/960,790 and 60/960,791, which are incorporated herein by reference. The food will be transported through a food passageway 16, defined as comprising all components which come into contact with the food, i.e. including the food reservoir 12, the inlet valve 14, the outlet valve 15, and the connectors 17 and 18. This food passageway is preferably manufactured of a biocompatible material. Preferably, the food reservoir 12 may be adapted to empty relatively slowly into the intestine. A food sensor 117 may be arranged outside of the food reservoir 12 on its inlet side in order to register when food is to arrive to the food reservoir 12. The food sensor 117 is e.g. arranged at the position shown in FIG. 4b, but may as has been earlier mentioned be situated e.g at the oesophagus wall (see FIG. 33). The registration that food is to arrive to the food reservoir 12 is e.g. made by registering change in volume of the oesophagus or change of the curvature or elongation of the oesophagus wall in which case the food sensor is preferably arranged on or at the oesophagus wall as shown in FIG. 33.

A food handling system 19 is connected to the food reservoir 12 is be adapted to handle the food in the food reservoir 12 mechanically and/or chemically. A mechanical food handling system may include at least one of: a moving system moving the food around in the food reservoir 12, a squeezing system squeezing the food in the food reservoir 12, a cutting system cutting the food in the food reservoir 12 (e.g. by rotating knives), or any other system suitable for mechanically handling the food in the food reservoir 12. On the other hand, a chemical food handling system may be adapted to release various chemicals into the food reservoir 12 for treating the food, e.g. by releasing digestion-facilitating chemicals (e.g. an enzyme, an acid, etc.), or disinfecting chemicals (e.g. an anti-bacterial substance) into the food. A cleaning system 20 is provided and may be adapted to treat the food passageway 16 with cleaning chemicals, e.g. including any anti-bacterial substance.

To enable the releasing of digestion-facilitating chemicals, disinfecting chemicals, or cleaning chemicals in the food reservoir 12, the artificial stomach 10 comprises a special container 21 adapted to accumulate these chemicals before distributing them to the food reservoir 12. Furthermore, an injection port 22 connected to the special container 21 is also provided to enable filling or re-filling of chemicals to the special container 21. The injection port 22 is adapted to be placed subcutaneously on the patient's body, and is further adapted to be injected with at least one of: an anti-bacterial liquid, an acid, a cleaning fluid, a contrast medium, or any other suitable liquid.

In order to operate the artificial stomach 10, an operating device 40 is provided. The operating device 40 may electrically and/or hydraulically operate the artificial stomach 10, e.g. by operating the food handling system 19, or the cleaning system 20. In the case when the artificial stomach 10 is electrically operated, the operation device 40 is electrically powered and may e.g. comprise an electrical motor. In the case when the artificial stomach 10 is hydraulically operated, the operation device 40 is instead a hydraulic operation device. However, a skilled person will understand that the operation device 40 may also be designed to be powered and operated in different ways. For instance, the food handling system 19 may be operated hydraulically, but be powered electrically.

The artificial stomach 10 is adapted for various functions, e.g. mechanically food handling, chemical food handling, or cleaning the food passage way 16, and at least one of the functions may be regulated from outside the patient's 200 body. For regulating a function from outside the patient's 200 body, a subcutaneous switch may be adapted to be pressed by the patient. Alternatively, when the artificial stomach 10 is hydraulically operated, a hydraulic reservoir having a connection with the hydraulic operation device 40 may be adapted to be manually pressed by the patient 200 for regulating the operation device 40. The hydraulic reservoir may be the special container 21, and may be placed invasively or non-invasively. When the operation device 40 is powered electrically, the artificial stomach 10 in one alternative may comprise an internal energy source (e.g. a battery or an accumulator), a remote control and a receiver for the information signals from the remote control. These components are adapted to enable for the patient to regulate the artificial stomach from outside the body. Different ways of controlling or regulating the artificial stomach will be described below with reference to FIGS. 9-32.

However, a skilled person will understand that the components of the described embodiment may be varied and he is also capable to construct an artificial stomach comprising various combinations of these components.

Figure 5:
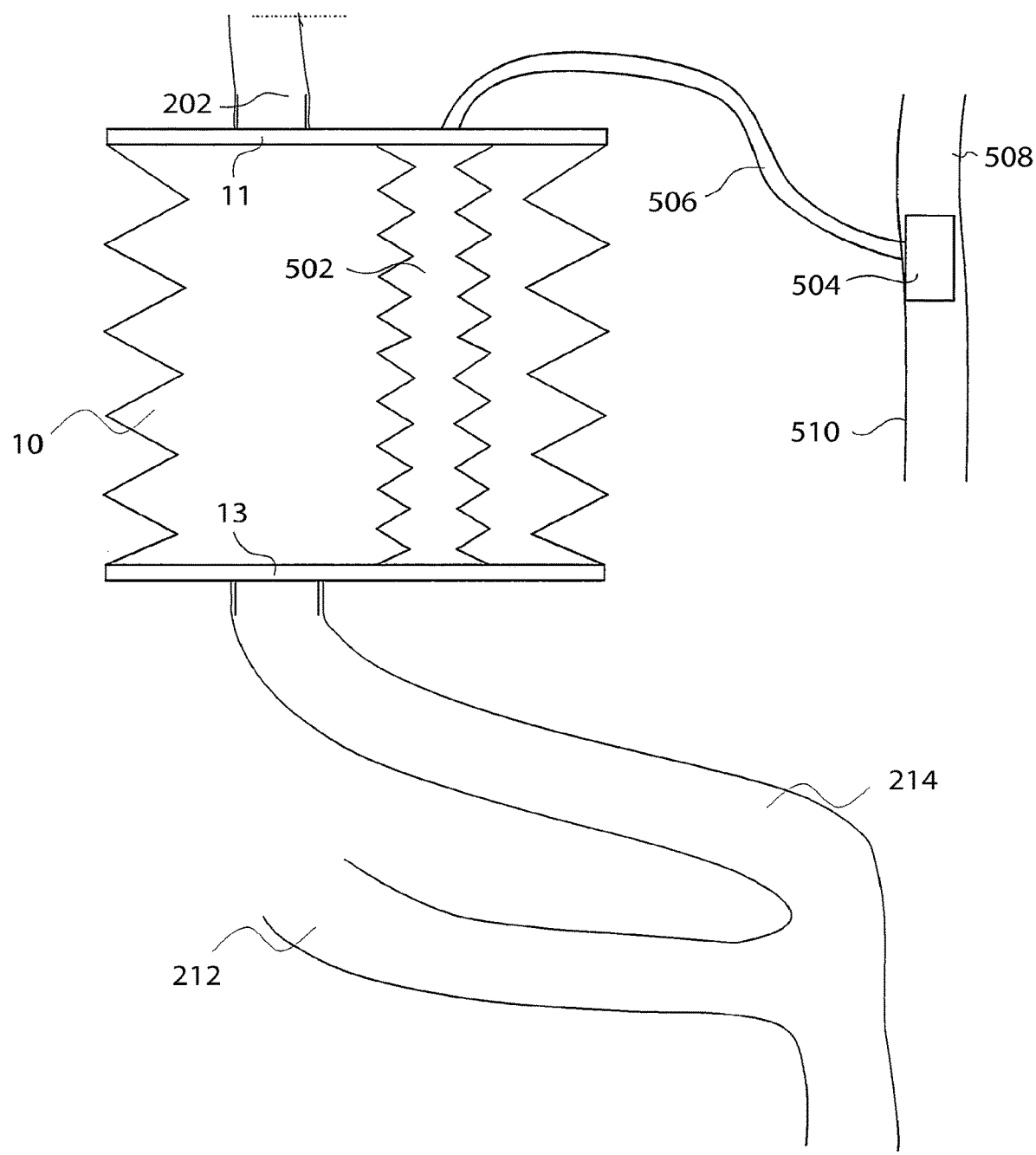
FIG. 5 is a drawing illustrating a hydraulically operated artificial stomach according to a further embodiment.
Figure 6:
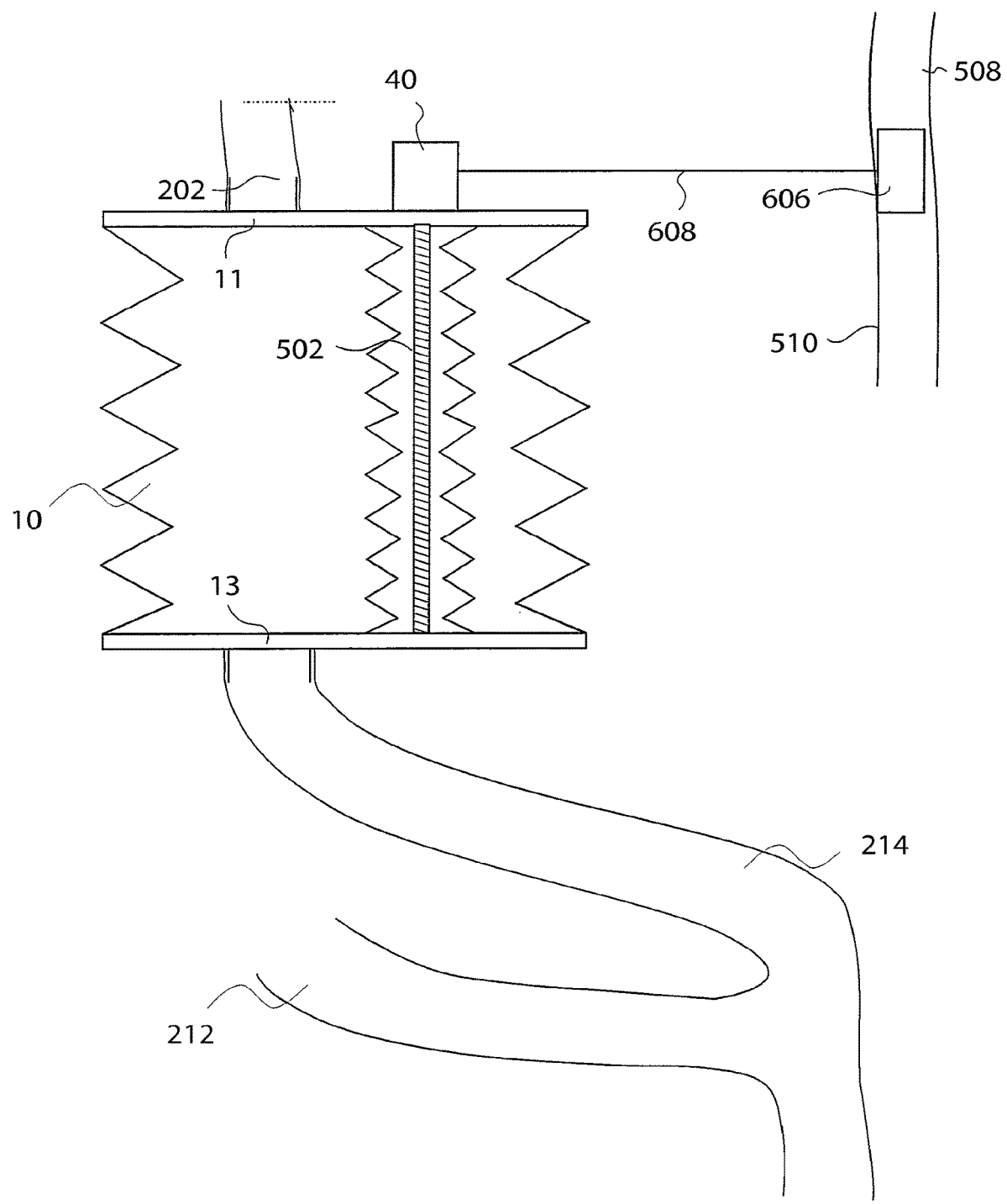
FIG. 6 is a drawing showing an electrically operated artificial stomach according to a yet further embodiment.

An artificial stomach in accordance with an exemplary embodiment of the present invention will now be described with reference to FIG. 5, and with further reference to FIG. 2 and FIG. 4. The artificial stomach 10 is preferably manufactured in order to have an anatomical structure similar to the structure of the normal stomach, and is adapted to be placed in the abdomen of a patient. In this embodiment the artificial stomach 10 is hydraulically operated. The artificial stomach 10 is connected to the gastrointestinal tract, upstream the inlet 11 is connected to the oesophagus 202 and downstream the outlet 13 is connected to the distal end of the cut jejunum 214. However, a skilled person will understand that the artificial stomach 10 may be implanted on various places of the gastrointestinal tract. For instance, a patient 200 having the stomach removed by the Roux-en-Y method, may have the remaining gastrointestinal tract (oesophagus 202 sutured with distal end of jejunum 214) cut and connected to the inlet 11 and outlet 13 of an artificial stomach 10. In that case, an upstream part of the jejunum 214 may be connected to the inlet 11 of the artificial stomach 10 and a downstream part of the jejunum 214 may be connected to the outlet 13 of the artificial stomach 10. A regulating bellow 502 of the artificial stomach 10 is connected through a hose 506 with a hydraulic reservoir, a servo reservoir, 504. The hydraulic reservoir 504 is placed subcutaneously in the patient 200, outside the abdominal wall 510, i.e. between the patient's skin 508 and the abdominal wall 510. The patient is then capable to operate the artificial stomach 10 by pressing or squeezing the hydraulic reservoir 504. Squeezing the hydraulic reservoir 504 will regulate the flow of hydraulic fluid to the regulating bellow 502. Alternatively, the hydraulic reservoir 504 may be placed on another suitable placement in the patient's 200 body and the squeezing of the hydraulic reservoir 504 may then be performed indirectly by e.g. pressing a subcutaneous switch, or activating a subcutaneously placed pump, etc. The switch and the pump may then be pressed and activated, respectively, by the patient 200. The food reservoir of the artificial stomach is optionally adapted to increase in volume when filled with food when the patient is eating, thereby causing a change in the volume of the servo reservoir, in turn moving fluid between said servo reservoir and said hydraulic fluid reservoir An artificial stomach in accordance with an exemplary embodiment of the present invention will now be described with reference to FIG. 6, and with further reference to FIG. 2 and FIG. 4. The artificial stomach 10 is manufactured in order to have an anatomical structure similar to the structure of the normal stomach, and is adapted to be placed in the abdomen of a patient. In this embodiment the artificial stomach 10 is mechanically operated. The artificial stomach 10 is connected to the gastrointestinal tract; upstream the inlet 11 is connected to the oesophagus 202 and downstream the outlet 13 is connected to the distal end of the cut jejunum 214. However, a skilled person will understand that the artificial stomach 10 may be implanted on various places of the gastrointestinal tract. For instance, a patient 200 having the stomach removed by the Roux.-en-Y method, may have the remaining gastrointestinal tract (oesophagus 202 sutured with distal end of jejunum 214) cut and connected to the inlet 11 and outlet 13 of an artificial stomach 10. In that case, an upstream part of the jejunum 214 may be connected to the inlet 11 of the artificial stomach 10 and a downstream part of the jejunum 214 may be connected to the outlet 13 of the artificial stomach 10. The artificial stomach 10 is regulated by a gear 74 driven by a motor 40. An operating unit 606, operating the motor 40 is placed subcutaneously in the patient 200, outside the abdominal wall 510, i.e. between the patient's skin 508 and the abdominal wall 510. The motor 40 is connected with the operating unit 606 and is also powered by the operating unit via a connector 608. The operating unit 606 may have a subcutaneous switch and the patient 200 is capable to operate the artificial stomach 10 by pressing the switch. Alternatively, the operating unit may be controlled by a remote control, or other suitable unit from outside the patient's 200 body. The food reservoir of the artificial stomach is optionally adapted to increase in volume when filled with food when the patient is eating, thereby causing a change in the gear 74 driven by the motor, e.g. by that the gear is allowed to move due to influence of the increase of food in the food reservoir. Said change also causes a change in the position of the bellow. According to this embodiment, the emptying of the food reservoir is direct or indirect regulated by a gear construction, preferably driven by a motor.

A connector (at 720) (earlier referred to as 17 and 18) in accordance with an exemplary embodiment of the present invention will now be described with reference to FIG. 7a and FIG. 7b, and with further reference to FIG. 3 and FIG. 4. The artificial stomach 10 comprises at least one connector (at 720) adapted to be connected to the oesophagus 202 or the intestine 204 of a patient. The connector (at 720) comprises a preferably circular conduit 726, which is fixedly attached at a first, proximal end on the outside the artificial stomach 10 and in fluid connection to the food passageway. The proximal part of the conduit 726 is formed like a tube 718, and distal to the tube 718 a bulge 728 is formed. A flexible sleeve 720 is rolled upon itself and then unrolled to cover part of the tube 718 and tubular tissue 722 (oesophagus 202 or intestine 204), which, in this case, is pulled over the second end 724 of the conduit 726 sufficiently far so as to extend also over the bulge 728. The flexible sleeve 720 has a structure adapted to facilitate in-growth of tissue through the flexible sleeve 720 to achieve a long term connection between the flexible sleeve 720 and the intestinal/oesophageal wall 722. After the flexible sleeve 720 has been unrolled over the tubular tissue 722, a blocking ring 730 is pushed over the flexible sleeve against the bulge 728. The ring 730 has an inner diameter less than the outer diameter of said bulge 728 but large enough to allow the intestinal/oesophageal wall 722 to be placed between said ring 730 and said tube 718, thereby adapted to stop said intestinal/oesophageal wall 722 to slip away from the tube 718. After a while, the threads 732 sutured to the intestinal/oesophageal wall 722 and the wall 734 of the conduit 726 (FIG. 7b) will have been absorbed by the patient's 200 body and, about during the same time, living tissue will have formed in and connected the intestinal/oesophageal wall 722 to the in-growth layer 736 of the flexible sleeve 720.

Therefore, as the intestinal/oesophageal wall 722 tends to be pulled off from the second end 724 of the conduit 726, the blocking ring 730 will also be moved, press the intestinal/oesophageal wall 722 and the flexible sleeve 720 against the bulge 728 and thereby prohibit any further slippage of the intestinal/oesophageal wall 722 over the bulge 728. The friction coefficient between the blocking ring 730 and the outer surface of the flexible sleeve 720 should be higher than the friction coefficient which the outer surface of the conduit's wall 734 has in relation to the intestinal/oesophageal wall 722. As has been described above, the connector (at 720) preferably comprises a flexible sleeve 720, but it is also possible as an option to leave out said sleeve 720 from the connector, in which case the blocking ring 730 is arranged with a somewhat smaller diameter compared to the one shown in FIGS. 7a and 7b in order to preserve the functionality described above.

System

An artificial stomach system, generally designated 28 and comprising an artificial stomach as described above will now be described with reference to FIGS. 8-32.

Figure 8:
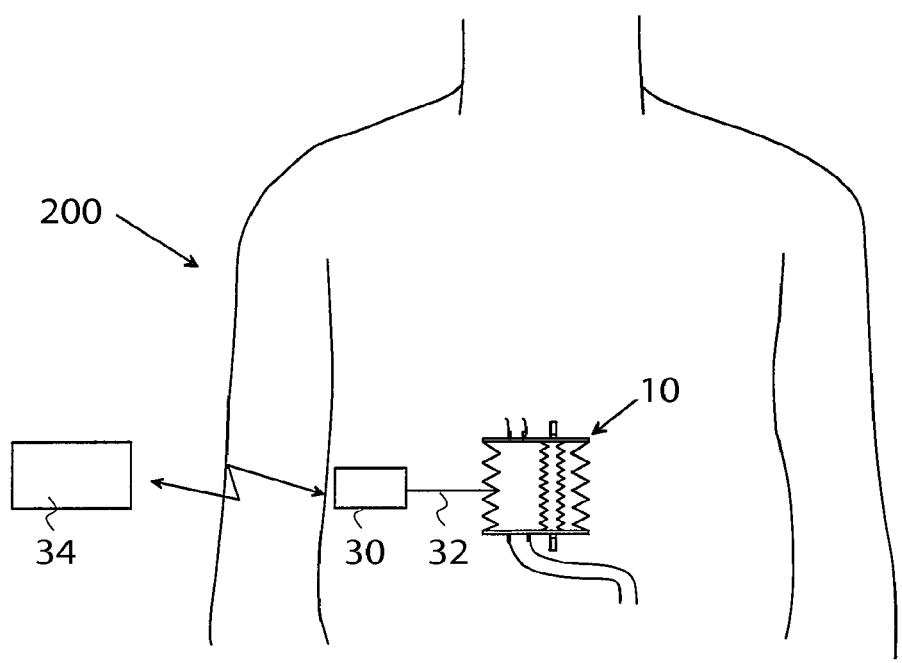
FIG. 8 is a drawing illustrating a system comprising an artificial stomach implanted in a patient in accordance with another embodiment.

The system of FIG. 8 comprises an artificial stomach 10 placed in the abdomen of the patient 200. An internal energy source in the form of an implanted energy transforming device 30 is adapted to supply energy consuming components of the artificial stomach system with energy via a power supply line 32. An external energy transmission device 34 includes a wireless remote control transmitting a wireless signal, which is received by a signal receiver which may be incorporated in the implanted energy transforming device 30 or be separated therefrom. The implanted energy transforming device 30 transforms energy from the signal into electric energy which is supplied via the power supply line 32.

Figure 9:
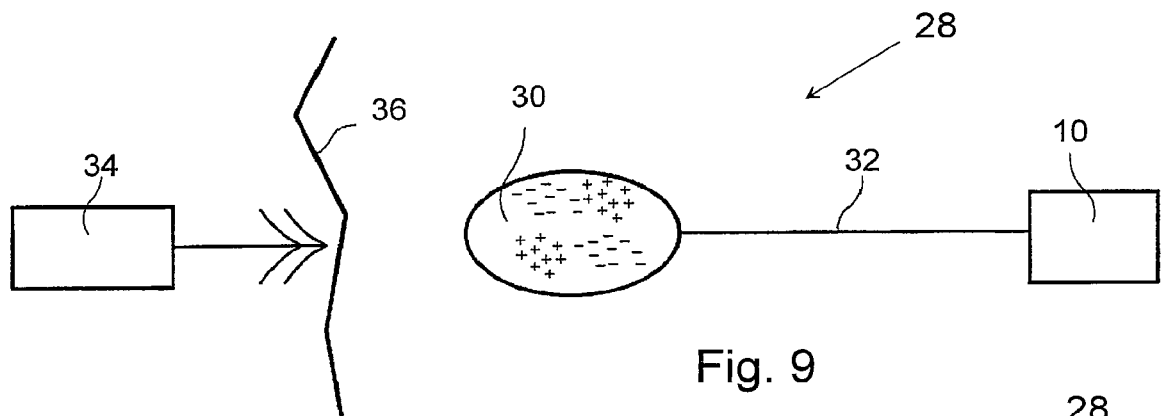
FIGS. 9-32c are schematic drawings of various embodiments of arrangements for powering and controlling the artificial stomach.

The system of FIG. 8 is shown in a more generalized block diagram form in FIG. 9, wherein the patient's skin 36, generally shown by a vertical line, separates the interior of the patient to the right of the line from the exterior to the left of the line.

Figure 10:
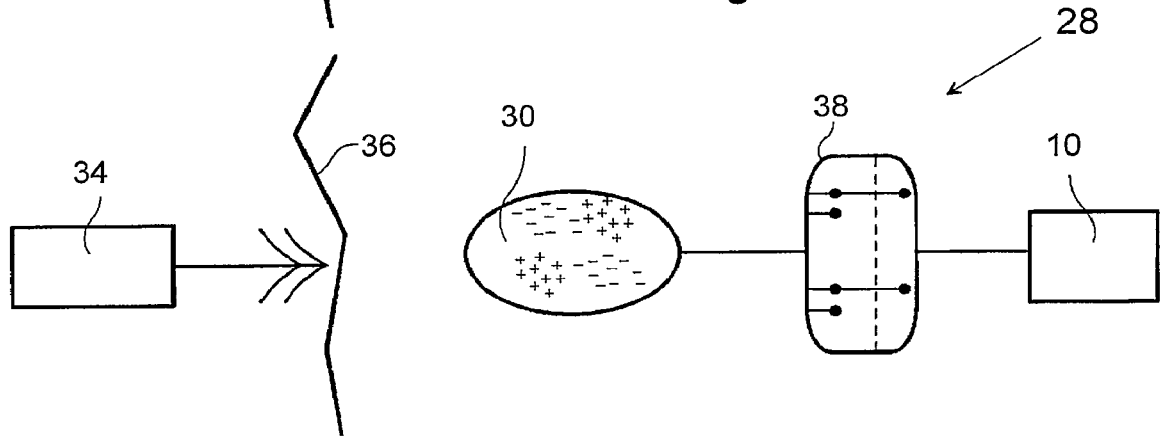

FIG. 10 shows an embodiment of the invention identical to that of FIG. 9, except that a reversing device in the form of an electric switch 38 operable by polarized energy also is implanted in the patient for reversing the artificial stomach 10. The wireless remote control of the external energy transmission device 34 transmits a wireless signal that carries polarized energy and the implanted energy transforming device 30 transforms the wireless polarized energy into a polarized current for operating the electric switch 38. When the polarity of the current is shifted by the implanted energy transforming device 30 the electric switch 38 reverses the function performed by the artificial stomach 10.

Figure 11:
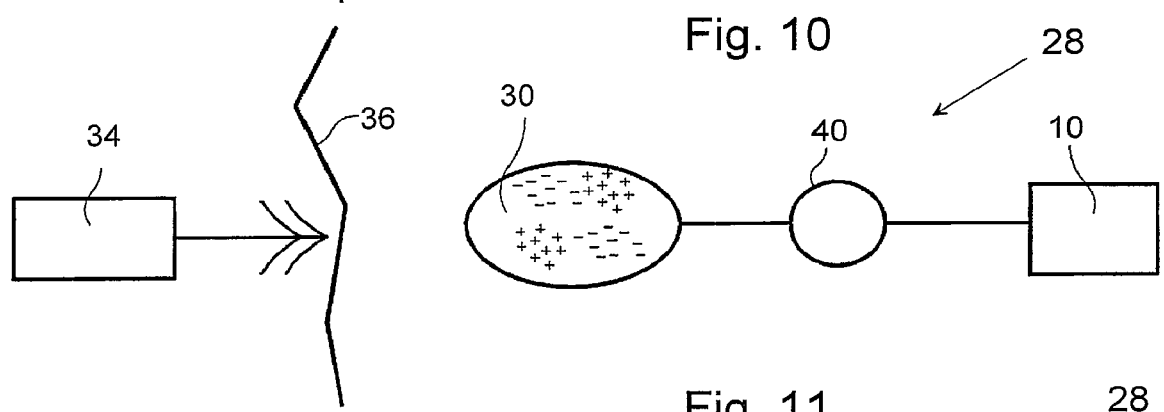

FIG. 11 shows an embodiment of the invention identical to that of FIG. 9, except that an operation device 40 implanted in the patient for regulating the artificial stomach 10 is provided between the implanted energy transforming device 30 and the artificial stomach 10. This operation device can be in the form of a motor 40, such as an electric servomotor. The motor 40 is powered with energy from the implanted energy transforming device 30, as the remote control of the external energy transmission device 34 transmits a wireless signal to the receiver of the implanted energy transforming device 30.

Figure 12:
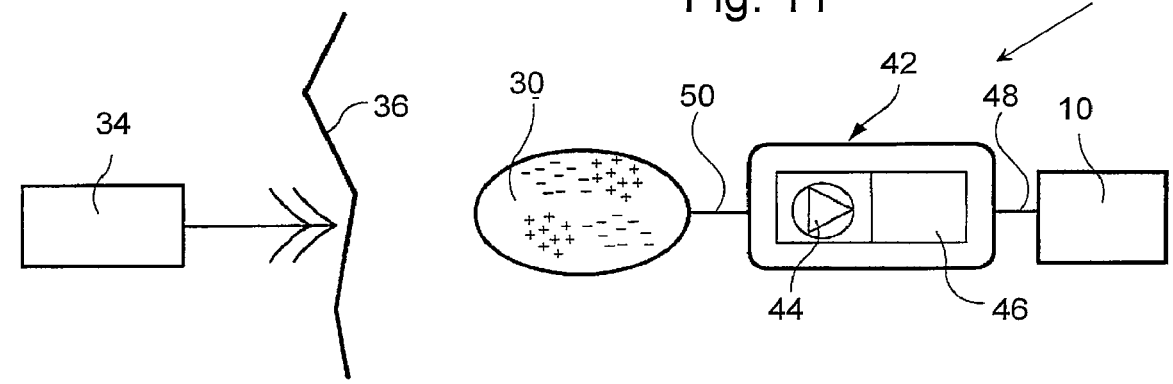

FIG. 12 shows an embodiment of the invention identical to that of FIG. 9, except that it also comprises an operation device is in the form of an assembly 42 including a motor/pump unit 78 and a regulation reservoir 46 is implanted in the patient. In this case the artificial stomach 10 is hydraulically operated, i.e. hydraulic fluid is pumped by the motor/pump unit 44 from the regulation reservoir 46 through a conduit 48 to the artificial stomach 10 to operate the artificial stomach, and hydraulic fluid is pumped by the motor/pump unit 44 back from the artificial stomach 10 to the regulation reservoir 46 to return the artificial stomach to a starting position. The implanted energy transforming device 30 transforms wireless energy into a current, for example a polarized current, for powering the motor/pump unit 44 via an electric power supply line 50.

Instead of a hydraulically operated artificial stomach 10, it is also envisaged that the operation device comprises a pneumatic operation device. In this case, pressurized air can be used for regulation and the regulation reservoir is replaced by an air chamber and the fluid is replaced by air.

In all of these embodiments the implanted energy transforming device 30 may include a rechargeable accumulator like a battery or a capacitor to be charged by the wireless energy and supplies energy for any energy consuming part of the device.

The external energy transmission device 34 is preferably wireless and may include a remotely controlled control device for controlling the device from outside the human body.

Such a control device may include a wireless remote control as well as a manual control of any implanted part to make contact with by the patient's hand most likely indirect for example a button to press placed under the skin.

Figure 13:
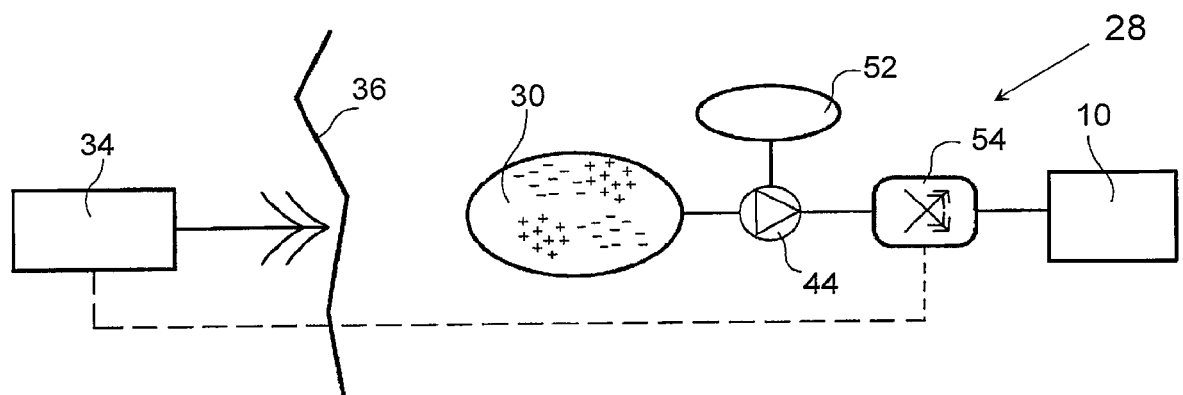

FIG. 13 shows an embodiment of the invention comprising the external energy transmission device 34 with its wireless remote control, the artificial stomach 10, in this case hydraulically operated, and the implanted energy transforming device 30, and further comprising a hydraulic fluid reservoir 52, a motor/pump unit 44 and an reversing device in the form of a hydraulic valve shifting device 54, all implanted in the patient. Of course the hydraulic operation could easily be performed by just changing the pumping direction and the hydraulic valve may therefore be omitted. The remote control may be a device separated from the external energy transmission or included in the same. The motor of the motor/pump unit 44 is an electric motor. In response to a control signal from the wireless remote control of the external energy transmission device 34, the implanted energy transforming device 30 powers the motor/pump unit 44 with energy from the energy carried by the control signal, whereby the motor/pump unit 44 distributes hydraulic fluid between the hydraulic fluid reservoir 52 and the artificial stomach 10. The remote control of the external energy transmission device 34 controls the hydraulic valve shifting device 54 to shift the hydraulic fluid flow direction between one direction in which the fluid is pumped by the motor/pump unit 44 from the hydraulic fluid reservoir 52 to the artificial stomach 10 to operate the artificial stomach, and another opposite direction in which the fluid is pumped by the motor/pump unit 44 back from the artificial stomach 10 to the hydraulic fluid reservoir 52 to return the artificial stomach to a starting position.

Figure 14:
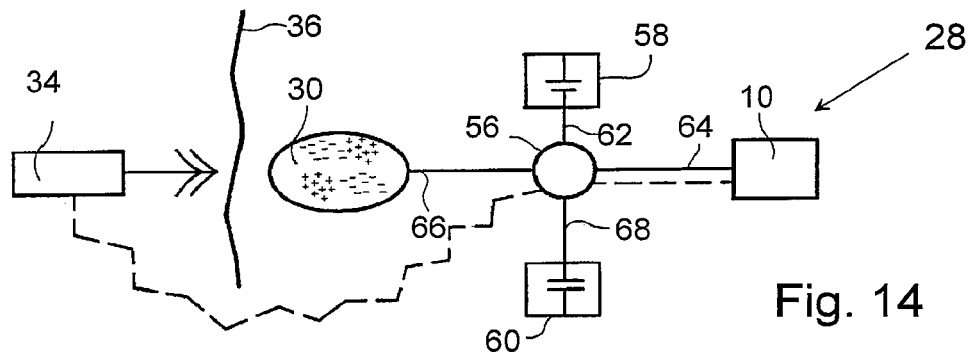

FIG. 14 shows an embodiment of the invention identical to that of FIG. 13, except that an internal control unit 56 controlled by the wireless remote control of the external energy transmission device 34, an accumulator 58 and a capacitor 60 also are implanted in the patient. The internal control unit 56 arranges storage of electric energy received from the implanted energy transforming device 30 in the accumulator 58, which supplies energy to the artificial stomach 10. In response to a control signal from the wireless remote control of the external energy transmission device 34, the internal control unit 56 either releases electric energy from the accumulator 58 and transforms the released energy via power lines 62 and 64, or directly transforms electric energy from the implanted energy transforming device 30 via a power line 66, the capacitor 60, which stabilizes the electric current, a power line 68 and the power line 64, for the operation of the artificial stomach 10.

The internal control unit is preferably programmable from outside the patient's body. In a preferred embodiment, the internal control unit is programmed to regulate the artificial stomach 10 to stretch the stomach according to a pre-programmed time-schedule or to input from any sensor sensing any possible physical parameter of the patient or any functional parameter of the device.

In accordance with an alternative, the capacitor 60 in the embodiment of FIG. 14 may be omitted. In accordance with another alternative, the accumulator 58 in this embodiment may be omitted.

Figure 15:
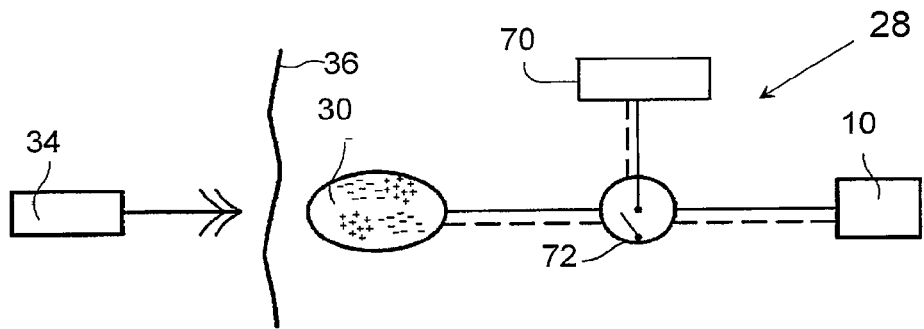

FIG. 15 shows an embodiment of the invention identical to that of FIG. 9, except that a battery 70 for supplying energy for the operation of the artificial stomach 10 and an electric switch 72 for switching the operation of the artificial stomach 10 also are implanted in the patient. The electric switch 72 is operated by the energy supplied by the implanted energy transforming device 30 to switch from an off mode, in which the battery 70 is not in use, to an on mode, in which the battery 70 supplies energy for the operation of the artificial stomach 10.

Figure 16:
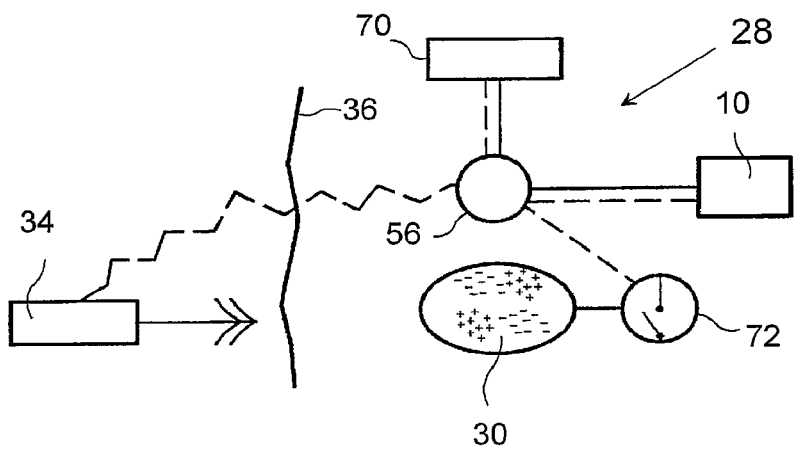

FIG. 16 shows an embodiment of the invention identical to that of FIG. 15, except that an internal control unit 56 controllable by the wireless remote control of the external energy transmission device 34 also is implanted in the patient. In this case, the electric switch 72 is operated by the energy supplied by the implanted energy transforming device 30 to switch from an off mode, in which the wireless remote control is prevented from controlling the internal control unit 56 and the battery is not in use, to a standby mode, in which the remote control is permitted to control the internal control unit 56 to release electric energy from the battery 70 for the operation of the artificial stomach 10.

Figure 17:
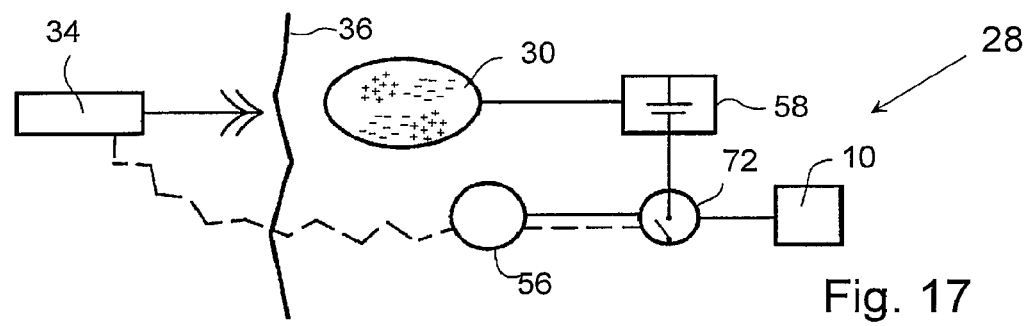

FIG. 17 shows an embodiment of the invention identical to that of FIG. 16, except that an accumulator 58 is substituted for the battery 70 and the implanted components are interconnected differently. In this case, the accumulator 58 stores energy from the implanted energy transforming device 30. In response to a control signal from the wireless remote control of the external energy transmission device 34, the internal control unit 56 controls the electric switch 72 to switch from an off mode, in which the accumulator 58 is not in use, to an on mode, in which the accumulator 58 supplies energy for the operation of the artificial stomach 10.

Figure 18:
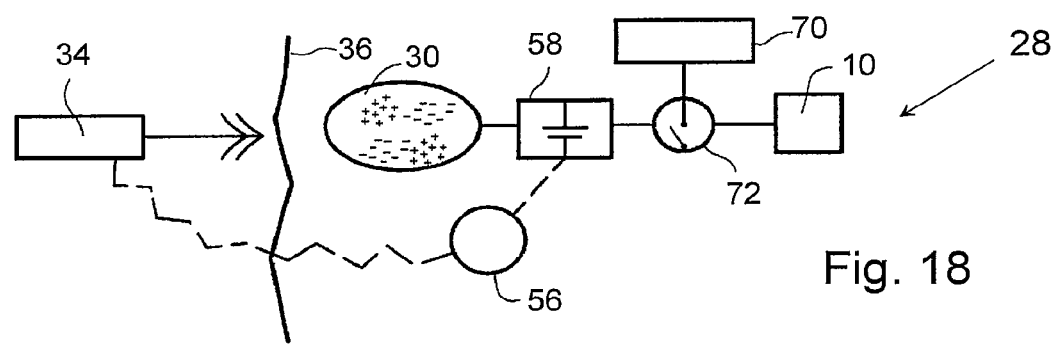

FIG. 18 shows an embodiment of the invention identical to that of FIG. 17, except that a battery 70 also is implanted in the patient and the implanted components are interconnected differently. In response to a control signal from the wireless remote control of the external energy transmission device 34, the internal control unit 56 controls the accumulator 58 to deliver energy for operating the electric switch 72 to switch from an off mode, in which the battery 70 is not in use, to an on mode, in which the battery 70 supplies electric energy for the operation of the artificial stomach 10.

Alternatively, the electric switch 72 may be operated by energy supplied by the accumulator 58 to switch from an off mode, in which the wireless remote control is prevented from controlling the battery 70 to supply electric energy and is not in use, to a standby mode, in which the wireless remote control is permitted to control the battery 70 to supply electric energy for the operation of the artificial stomach 10.

It should be understood that the switch should be interpreted in its broadest embodiment. This means an Field-programmable gate array (FPGA) or a D/A converter or any other electronic component or circuit may switch power on and off preferably being controlled from outside the body or by an internal control unit.

Figure 19:
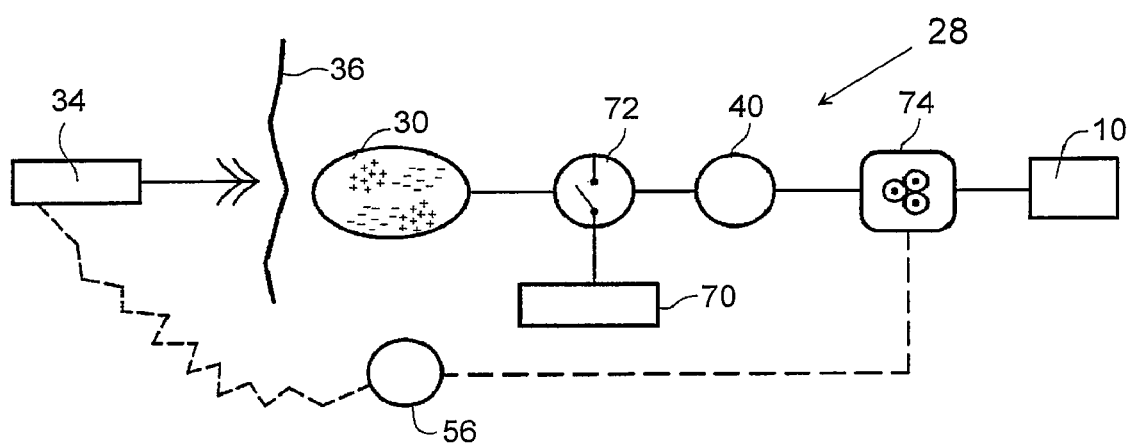

FIG. 19 shows an embodiment of the invention identical to that of FIG. 15, except that a motor 40, a mechanical reversing device in the form of a gear 74, and an internal control unit 56 for controlling the gear 74 also are implanted in the patient. The internal control unit 56 controls the gear 74 to reverse the function performed by the artificial stomach 10 (mechanically operated). Even simpler is to switch the direction of the motor electronically.

Figure 20:
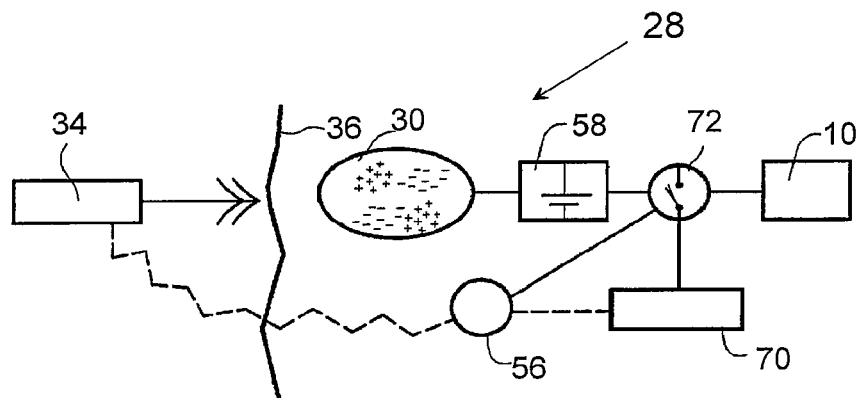

FIG. 20 shows an embodiment of the invention identical to that of FIG. 20 except that the implanted components are interconnected differently. Thus, in this case the internal control unit 56 is powered by the battery 70 when the accumulator 58, suitably a capacitor, activates the electric switch 72 to switch to an on mode. When the electric switch 72 is in its on mode the internal control unit 56 is permitted to control the battery 70 to supply, or not supply, energy for the operation of the artificial stomach 10.

Figure 21:
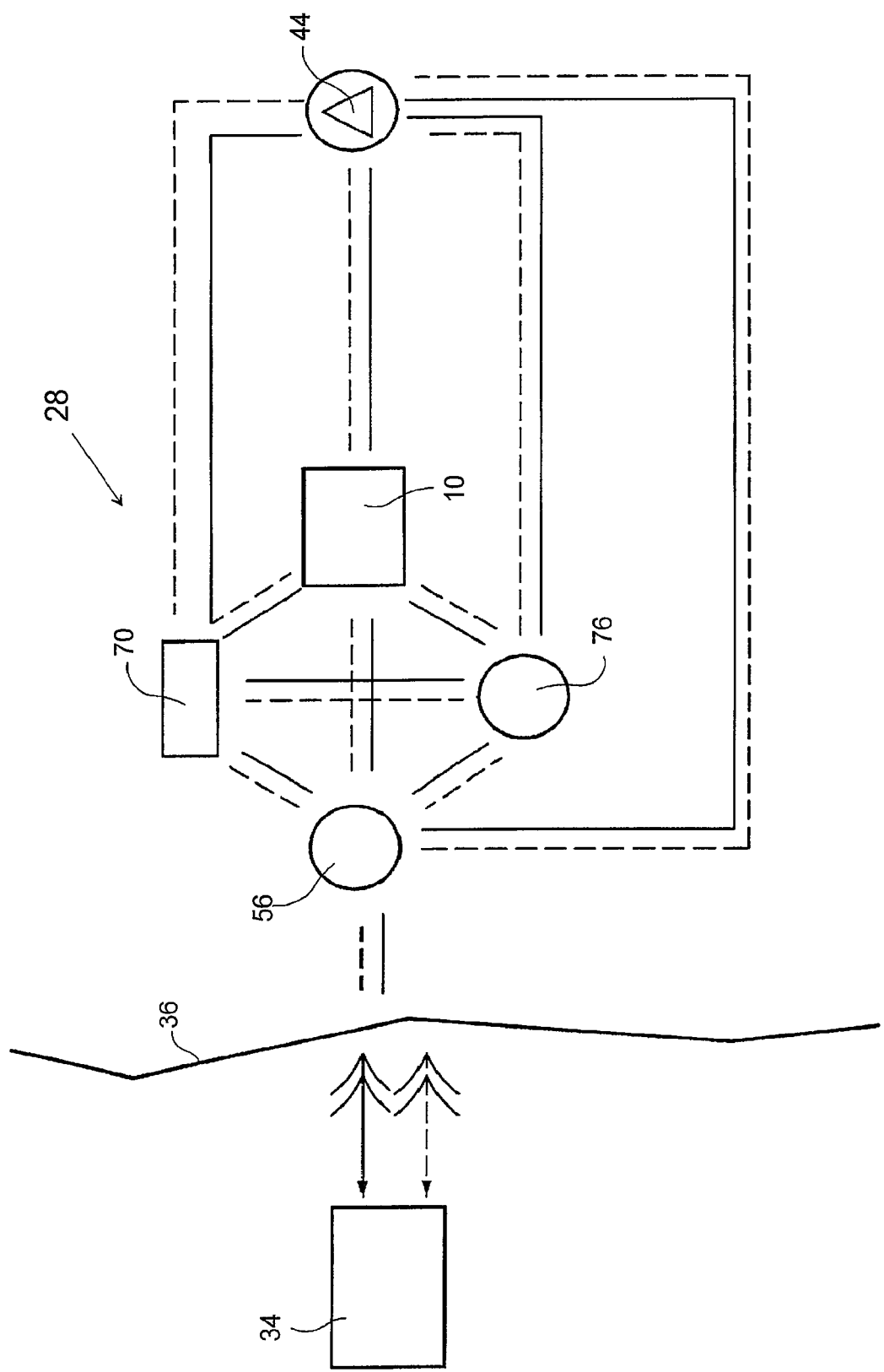
Figure 22:
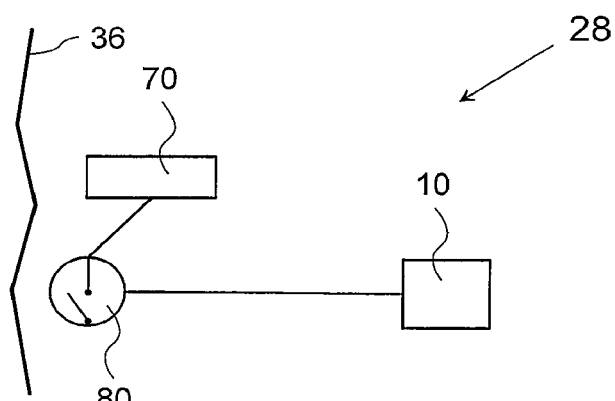

FIG. 21 schematically shows conceivable combinations of implanted components of the apparatus for achieving various communication options. Basically, there are the artificial stomach 10, the internal control unit 56, motor or pump unit 44, and the external energy transmission device 34 including the external wireless remote control. As already described above the wireless remote control transmits a control signal which is received by the internal control unit 56, which in turn controls the various implanted components of the apparatus.

A feedback device, preferably in the form of a sensor 76, may be implanted in the patient for sensing a physical parameter of the patient, such as a contraction wave in the oesophagus informing the patient is eating. The internal control unit 56, or alternatively the external wireless remote control of the external energy transmission device 34, may control the artificial stomach 10 in response to signals from the sensor 76. A transceiver may be combined with the sensor 76 for sending information on the sensed physical parameter to the external wireless remote control. The wireless remote control may comprise a signal transmitter or transceiver and the internal control unit 56 may comprise a signal receiver or transceiver. Alternatively, the wireless remote control may comprise a signal receiver or transceiver and the internal control unit 56 may comprise a signal transmitter or transceiver. The above transceivers, transmitters and receivers may be used for sending information or data related to the artificial stomach 10 from inside the patient's body to the outside thereof.

Alternatively, the sensor 76 may be arranged to sense a functional parameter of the artificial stomach 10.

Where the motor/pump unit 44 and battery 70 for powering the motor/pump unit 44 are implanted, the battery 70 may be equipped with a transceiver for sending information on the condition of the battery 70. To be more precise, when charging a battery or accumulator with energy feed back information related to said charging process is sent and the energy supply is changed accordingly.

FIG. 21 shows an alternative embodiment wherein the artificial stomach 10 is regulated from outside the patient's body. The artificial stomach system 28 comprises an artificial stomach 10 connected to a battery 70 via a subcutaneous switch 80. Thus, the regulation of the artificial stomach 10 is performed non-invasively by manually pressing the subcutaneous switch, whereby the operation of the artificial stomach 10 is switched on and off. It will be appreciated that the shown embodiment is a simplification and that additional components, such as an internal control unit or any other part disclosed in the present application can be added to the artificial stomach system.

Figure 23:
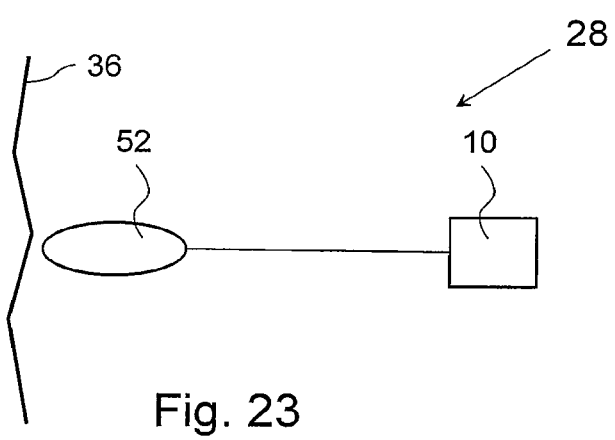

FIG. 23 shows an alternative embodiment, wherein the artificial stomach system 28 comprises an artificial stomach 10 in fluid connection with a hydraulic fluid reservoir 52. Non-invasive regulation is performed by manually pressing the hydraulic reservoir connected to the artificial stomach 10.

A further embodiment of a system according to the invention comprises a feedback device for sending information from inside the patient's body to the outside thereof to give feedback information related to at least one functional parameter of the artificial stomach or system or a physical parameter of the patient, thereby optimizing the performance of the system.

One preferred functional parameter of the device is correlated to the transfer of energy for charging the internal energy source.

Figure 24:
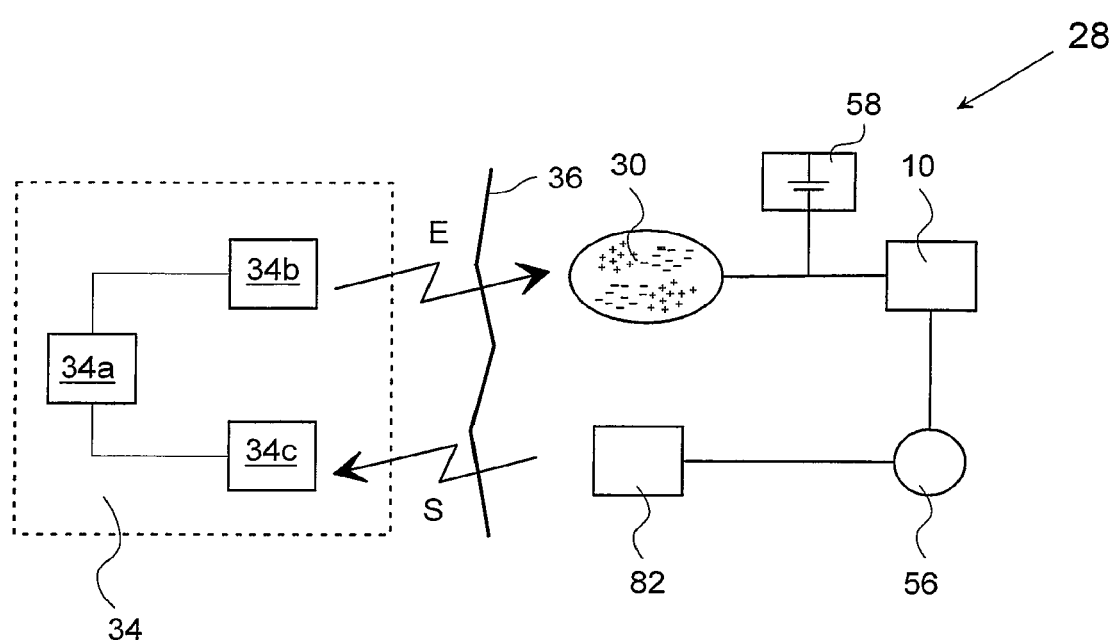

In FIG. 24, an arrangement is schematically illustrated for supplying an accurate amount of energy to an artificial stomach system 28 implanted in a patient, whose skin 36 is indicated by a vertical line. An artificial stomach 10 is connected to an implanted energy transforming device 30, likewise located inside the patient, preferably just beneath the patient's skin 36. Generally speaking, the implanted energy transforming device 30 may be placed in the abdomen, thorax, muscle fascia (e.g. in the abdominal wall), subcutaneously, or at any other suitable location. The the implanted energy transforming device 30 is adapted to receive wireless energy E transmitted from an external energy source 34a provided in the external energy transmission device 34 located outside the patient's skin 36 in the vicinity of the implanted energy transforming device 30.

As is well known in the art, the wireless energy E may generally be transferred by means of any suitable Transcutaneous Energy Transfer (TET) device, such as a device including a primary coil arranged in the external energy source 34a and an adjacent secondary coil arranged in the implanted energy transforming device 30. When an electric current is fed through the primary coil, energy in the form of a voltage is induced in the secondary coil which can be used to operate an artificial stomach, e.g. after storing the incoming energy in an energy storing device or accumulator, such as a battery or a capacitor. However, the present invention is generally not limited to any particular energy transfer technique, TET devices or energy storing devices, and any kind of wireless energy may be used.

The amount of energy received inside the body to the device may be compared with the energy used by the device. The term used by the device is then understood to include also energy stored by the device. The amount of transferred energy can be regulated by means of an external control unit 34b controlling the external energy source 34a based on the determined energy balance, as described above. In order to transfer the correct amount of energy, the energy balance and the required amount of energy can be determined by means of an internal control unit 56 connected to the artificial stomach 10. The internal control unit 56 may thus be arranged to receive various measurements obtained by suitable sensors or the like, not shown, measuring certain characteristics of the artificial stomach 10, somehow reflecting the required amount of energy needed for proper operation of the artificial stomach 10. Moreover, the current condition of the patient may also be detected by means of suitable measuring devices or sensors, in order to provide parameters reflecting the patient's condition. Hence, such characteristics and/or parameters may be related to the current state of the artificial stomach 10, such as power consumption, operational mode and temperature, as well as the patient's condition reflected by, e.g., body temperature, blood pressure, heartbeats and breathing.

Furthermore, an energy storing device or accumulator 58 may optionally be connected to the implanted energy transforming device 30 for accumulating received energy for later use by the artificial stomach 10. Alternatively or additionally, characteristics of such an accumulator, also reflecting the required amount of energy, may be measured as well. The accumulator may be replaced by a battery, and the measured characteristics may be related to the current state of the battery, such as voltage, temperature, etc. In order to provide sufficient voltage and current to the artificial stomach 10, and also to avoid excessive heating, it is clearly understood that the battery should be charged optimally by receiving a correct amount of energy from the implanted energy transforming device 30, i.e. not too little or too much. The accumulator may also be a capacitor with corresponding characteristics.

For example, battery characteristics may be measured on a regular basis to determine the current state of the battery, which then may be stored as state information in a suitable storage means in the internal control unit 56. Thus, whenever new measurements are made, the stored battery state information can be updated accordingly. In this way, the state of the battery can be "calibrated" by transferring a correct amount of energy, so as to maintain the battery in an optimal condition.

Thus, the internal control unit 56 is adapted to determine the energy balance and/or the currently required amount of energy, (either energy per time unit or accumulated energy) based on measurements made by the above-mentioned sensors or measuring devices on the artificial stomach 10, or the patient, or an energy storing device if used, or any combination thereof. The internal control unit 56 is further connected to an internal signal transmitter 82, arranged to transmit a control signal reflecting the determined required amount of energy, to an external signal receiver 34c connected to the external control unit 34b. The amount of energy transmitted from the external energy source 34a may then be regulated in response to the received control signal.

Alternatively, sensor measurements can be transmitted directly to the external control unit 34b wherein the energy balance and/or the currently required amount of energy can be determined by the external control unit 34b, thus integrating the above-described function of the internal control unit 56 in the external control unit 34b. In that case, the internal control unit 56 can be omitted and the sensor measurements are supplied directly to the internal signal transmitter 82 which sends the measurements over to the external signal receiver 34c and the external control unit 34b. The energy balance and the currently required amount of energy can then be determined by the external control unit 34b based on those sensor measurements.

Hence, the present solution employs the feed back of information indicating the required energy, which is more efficient than previous solutions because it is based on the actual use of energy that is compared to the received energy, e.g. with respect to the amount of energy, the energy difference, or the energy receiving rate as compared to the energy rate used by the artificial stomach. The artificial stomach may use the received energy either for consuming or for storing the energy in an energy storage device or the like. The different parameters discussed above would thus be used if relevant and needed and then as a tool for determining the actual energy balance. However, such parameters may also be needed per se for any actions taken internally to specifically operate the artificial stomach.

The internal signal transmitter 82 and the external signal receiver 34c may be implemented as separate units using suitable signal transfer means, such as radio, IR (Infrared) or ultrasonic signals. Alternatively, the internal signal transmitter 82 and the external signal receiver 34c may be integrated in the implanted energy transforming device 30 and the external energy source 34a, respectively, so as to convey control signals in a reverse direction relative to the energy transfer, basically using the same transmission technique. The control signals may be modulated with respect to frequency, phase or amplitude.

To conclude, the energy supply arrangement illustrated in FIG. 24 may operate basically in the following manner. The energy balance is first determined by the internal control unit 56. A control signal reflecting the required amount of energy is also created by the internal control unit 56, and the control signal is transmitted from the internal signal transmitter 82 to the external signal receiver 34c. Alternatively, the energy balance can be determined by the external control unit 34b instead depending on the implementation, as mentioned above. In that case, the control signal may carry measurement results from various sensors. The amount of energy emitted from the external energy source 34a can then be regulated by the external control unit 34b, based on the determined energy balance, e.g. in response to the received control signal. This process may be repeated intermittently at certain intervals during ongoing energy transfer, or may be executed on a more or less continuous basis during the energy transfer.

The amount of transferred energy can generally be regulated by adjusting various transmission parameters in the external energy source 34a, such as voltage, current, amplitude, wave frequency and pulse characteristics.

A method is thus provided for controlling transmission of wireless energy supplied to an electrically operable artificial stomach implanted in a patient. The wireless energy E is transmitted from an external energy source located outside the patient and is received by an internal energy receiver located inside the patient, the internal energy receiver being connected to the artificial stomach for directly or indirectly supplying received energy thereto. An energy balance is determined between the energy received by the internal energy receiver and the energy used for the artificial stomach. The transmission of wireless energy E from the external energy source is then controlled based on the determined energy balance.

A system is also provided for controlling transmission of wireless energy supplied to an electrically operable artificial stomach implanted in a patient. The system is adapted to transmit the wireless energy E from an external energy source located outside the patient which is received by an implanted energy transforming device located inside the patient, the implanted energy transforming device being connected to the artificial stomach for directly or indirectly supplying received energy thereto. The system is further adapted to determine an energy balance between the energy received by the implanted energy transforming device and the energy used for the artificial stomach, and control the transmission of wireless energy E from the external energy source, based on the determined energy balance.

The functional parameter of the device is correlated to the transfer of energy for charging the internal energy source.

In yet an alternative embodiment, the external source of energy is controlled from outside the patient's body to release electromagnetic wireless energy, and released electromagnetic wireless energy is used for operating the artificial stomach.

In another embodiment, the external source of energy is controlling from outside the patient's body to release non-magnetic wireless energy, and released non-magnetic wireless energy is used for operating the artificial stomach.

Those skilled in the art will realize that the above various embodiments according to FIGS. 13-25 could be combined in many different ways. For example, the electric switch 38 operated polarized energy could be incorporated in any of the embodiments of FIGS. 11, 14-20, the hydraulic valve shifting device 54 could be incorporated in the embodiment of FIG. 12, and the gear 74 could be incorporated in the embodiment of FIG. 11. Please observe that the switch simply could mean any electronic circuit or component.

Figure 25:
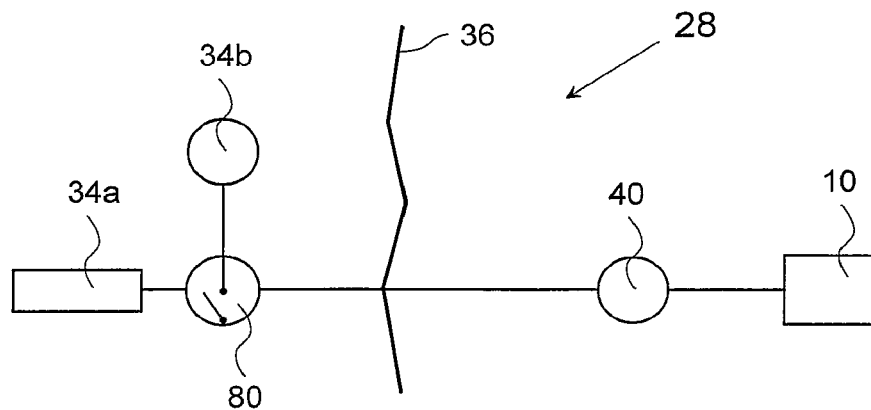

Wireless transfer of energy for operating the artificial stomach has been described to enable non-invasive operation. It will be appreciated that the artificial stomach can be operated with wire bound energy as well. On such example is shown in FIG. 25, wherein an external switch 84 is interconnected between the external energy source 34a and an operation device, such as an electric motor regulating the artificial stomach 10, by means of power lines 86 and 88. An external control unit 34b controls the operation of the external switch to effect proper operation of the artificial stomach 10.

Hydraulic or Pneumatic Powering

FIGS. 26-29 show in more detail block diagrams of four different ways of hydraulically or pneumatically powering an artificial stomach according to the invention.

Figure 26:
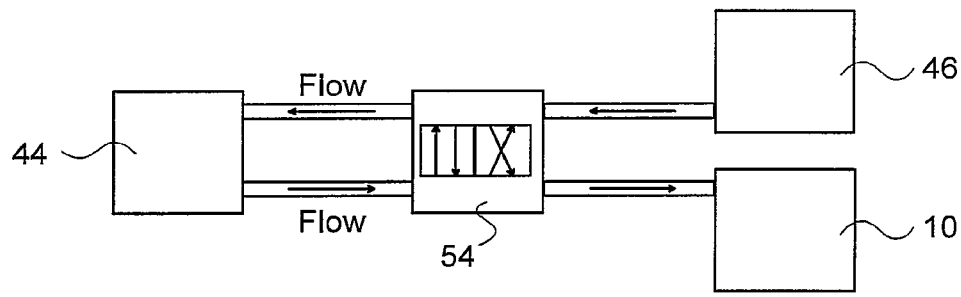

FIG. 26 shows an artificial stomach system as described above. The system comprises an artificial stomach 10 and further a separate regulation reservoir 46, a one way pump 44 and an alternate valve 54.

Figure 27:
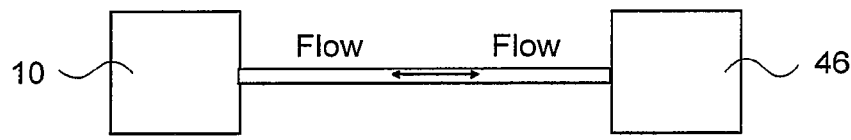

FIG. 27 shows the artificial stomach 10 and a regulation reservoir 46. By moving the wall of the regulation reservoir or changing the size of the same in any other different way, the adjustment of the artificial stomach may be performed without any valve, just free passage of fluid any time by moving the reservoir wall.

Figure 28:
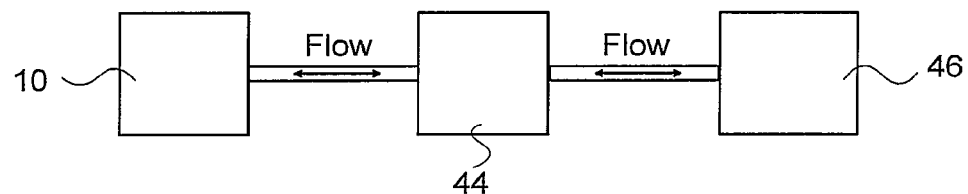

FIG. 28 shows the artificial stomach 10, a two way pump 44 and the regulation reservoir 46.

Figure 29:
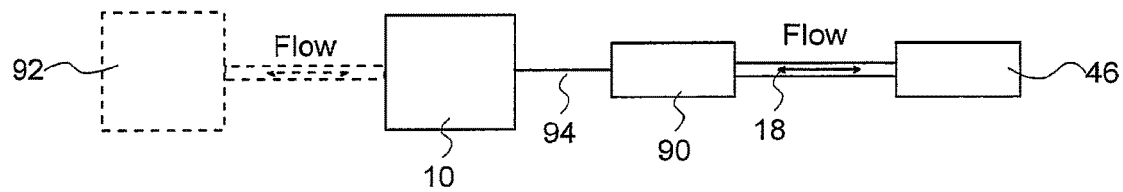

FIG. 29 shows a block diagram of a reversed servo system with a first closed system controlling a second closed system. The servo system comprises a regulation reservoir 46 and a servo reservoir 90. The servo reservoir 90 mechanically controls an artificial stomach 10 via a mechanical interconnection 94. The artificial stomach has an expandable/contactable cavity. This cavity is preferably expanded or contracted by supplying hydraulic fluid from the larger adjustable reservoir 92 in fluid connection with the artificial stomach 10. Alternatively, the cavity contains compressible gas, which can be compressed and expanded under the control of the servo reservoir 90.

The servo reservoir 90 can also be part of the artificial stomach itself.

Figure 30A:
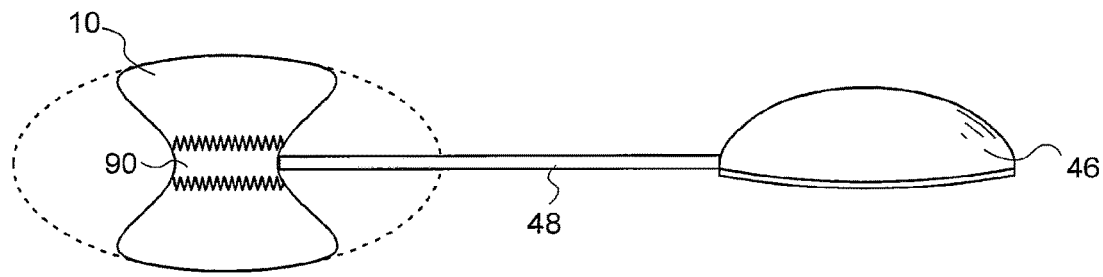
Figure 30B:
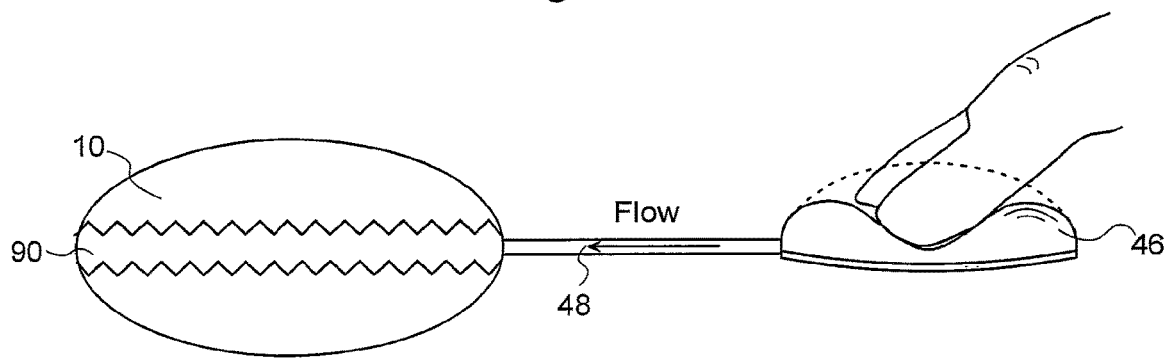
Figure 30C:
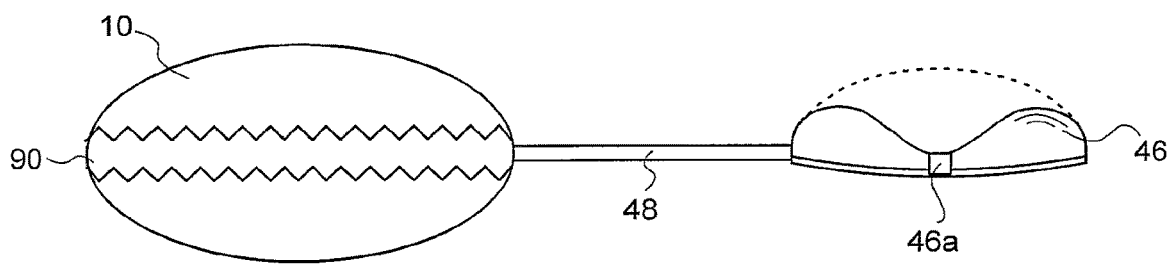
Figure 31:
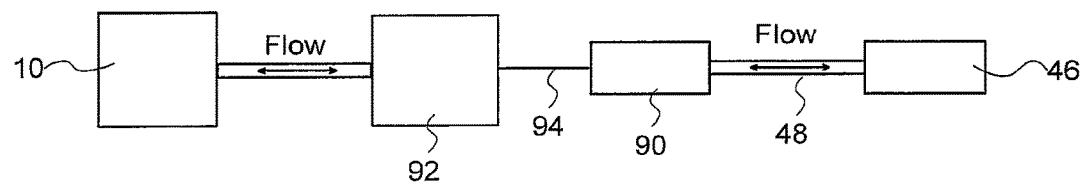

In one embodiment, the regulation reservoir is placed subcutaneous under the patient's skin and is operated by pushing the outer surface thereof by means of a finger. This artificial stomach system is illustrated in FIGS. 30a-c. In FIG. 30a, a flexible subcutaneous regulation reservoir 46 is shown connected to a bulge shaped servo reservoir 90 by means of a conduit 48. This bellow shaped servo reservoir 90 is comprised in a a flexible artificial stomach 10. In the state shown in FIG. 30a, the servo reservoir 90 contains a minimum of fluid and most fluid is found in the regulation reservoir 46. Due to the mechanical interconnection between the servo reservoir 90 and the artificial stomach 10, the outer shape of the artificial stomach 10 is contracted, i.e., it occupies less than its maximum volume. This maximum volume is shown with dashed lines in the Fig.

FIG. 30b shows a state wherein a user, such as the patient in with the artificial stomach is implanted, presses the regulation reservoir 46 so that fluid contained therein is brought to flow through the conduit 48 and into the servo reservoir 90, which, thanks to its bellow shape, expands longitudinally. This expansion in turn expands the artificial stomach 10 so that it occupies its maximum volume, thereby stretching the stomach wall (not shown), which it contacts.

The regulation reservoir 46 is preferably provided with means 46a for keeping its shape after compression. This means, which is schematically shown in the Fig., will thus keep the artificial stomach 10 in a stretched position also when the user releases the regulation reservoir. In this way, the regulation reservoir essentially operates as an on/off switch for the artificial stomach system.

An alternative embodiment of hydraulic or pneumatic operation will now be described with reference to FIGS. 32 and 33a-c. The block diagram shown in FIG. 31 comprises with a first closed system controlling a second closed system. The first system comprises a regulation reservoir 46 and a servo reservoir 90. The servo reservoir 90 mechanically controls a larger adjustable reservoir 92 via a mechanical interconnection 94. An artificial stomach 10 having an expandable/contactable cavity is in turn controlled by the larger adjustable reservoir 92 by supply of hydraulic fluid from the larger adjustable reservoir 92 in fluid connection with the artificial stomach 10.

Figure 32A:
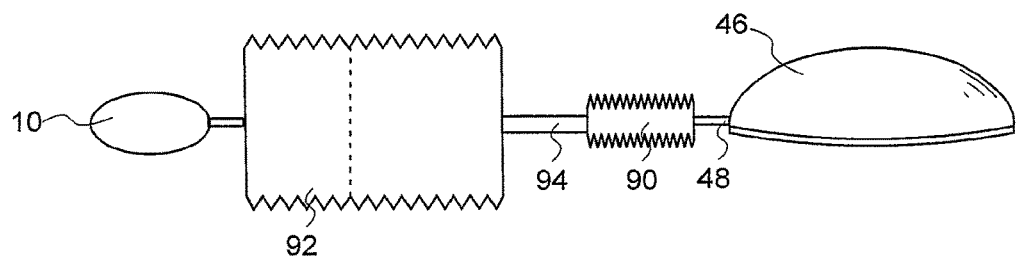
Figure 32B:
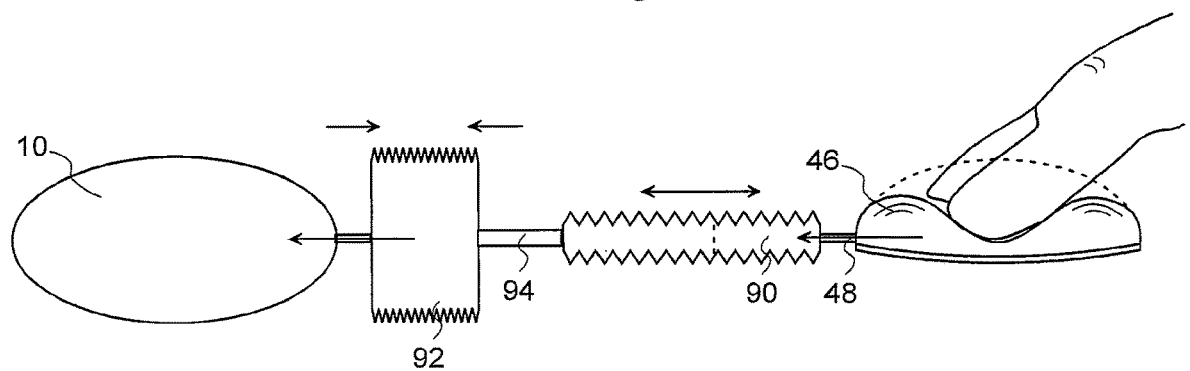
Figure 32C:
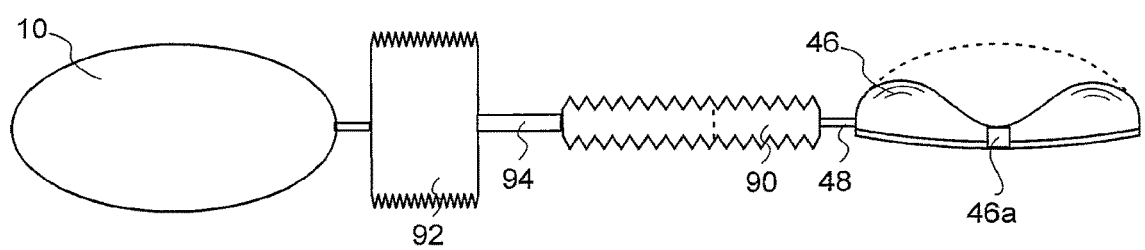

An example of this embodiment will now be described with reference to FIG. 32a-c. Like in the previous embodiment, the regulation reservoir is placed subcutaneous under the patient's skin and is operated by pushing the outer surface thereof by means of a finger. The regulation reservoir 46 is in fluid connection with a bellow shaped servo reservoir 90 by means of a conduit 48. In the first closed system comprising parts 46, 48, 90 shown in FIG. 30a, the servo reservoir 90 contains a minimum of fluid and most fluid is found in the regulation reservoir 46.

The servo reservoir 90 is mechanically connected to a larger adjustable reservoir 92, in this example also having a bellow shape but with a larger diameter than the servo reservoir 90. The larger adjustable reservoir 92 is in fluid connection with the artificial stomach 10. This means that when a user pushes the regulation reservoir 46, thereby displacing fluid from the regulation reservoir 46 to the servo reservoir 90, the expansion of the servo reservoir 90 will displace a larger volume of fluid from the larger adjustable reservoir 92 to the artificial stomach 10. In other words, in this reversed servo, a small volume in the regulation reservoir is compressed with a higher force and this creates a movement of a larger total area with less force per area unit.

Like in the previous embodiment described above with reference to FIGS. 31a-c, the regulation reservoir 46 is preferably provided with means 46a for keeping its shape after compression. This means, which is schematically shown in the Fig., will thus keep the artificial stomach 10 in a stretched position also when the user releases the regulation reservoir. In this way, the regulation reservoir essentially operates as an on/off switch for the artificial stomach system.

An artificial stomach in accordance with an exemplary embodiment of the present invention will now be described with reference to FIG. 33, and with further reference to FIGS. 2, 4a-b and 30a-c. The artificial stomach 10 is preferably manufactured in order to have an anatomical structure similar to the structure of the normal stomach, and is adapted to be placed in the abdomen of a patient. In this embodiment the artificial stomach 10 is hydraulically operated. The artificial stomach 10 is connected to the gastrointestinal tract, upstream the inlet 11 is connected to the oesophagus 202 and downstream the outlet 13 is connected to the distal end of the cut jejunum 214.

The artificial stomach 10 has a stomach food part, which is enclosed by an outer wall 550 manufactured from a rigid material. This rigid outer wall encloses two reservoirs: a food reservoir 12 and a servo reservoir 90, which are separated by a flexible inner wall 552. A hydraulic fluid reservoir 52 is separated from the stomach food part by the rigid outer wall 550 and is further enclosed by a fluid reservoir wall 556, which fluid reservoir wall 556 preferably is flexible but may as an option be rigid. If the fluid reservoir wall 556 is flexible, it may be arranged to flex in a way similar to that of the regulation reservoir wall 46 shown in FIGS. 30a and 30b.

The food reservoir 12 is adapted to receive and treat the food mechanically and/or chemically. The hydraulic fluid reservoir 52 is adapted to comprise a hydraulic fluid to be fed through conduits 44a, 44b to the servo reservoir 90. A pump 44 connected to the conduits 44a and 44b is adapted to move the hydraulic fluid between the hydraulic fluid reservoir 52 and the servo reservoir 90.

By manufacturing the walls 550, 552, 554, and 556 of materials of the above defined qualities and employing the pump 44 to feed the hydraulic fluid between the hydraulic fluid reservoir 52 and the servo reservoir 90 in an alternating direction, a mechanical treatment is achieved by squeezing the food in the food reservoir 12, as will now be described with reference to FIGS. 4b and 33.

Figure 4B:
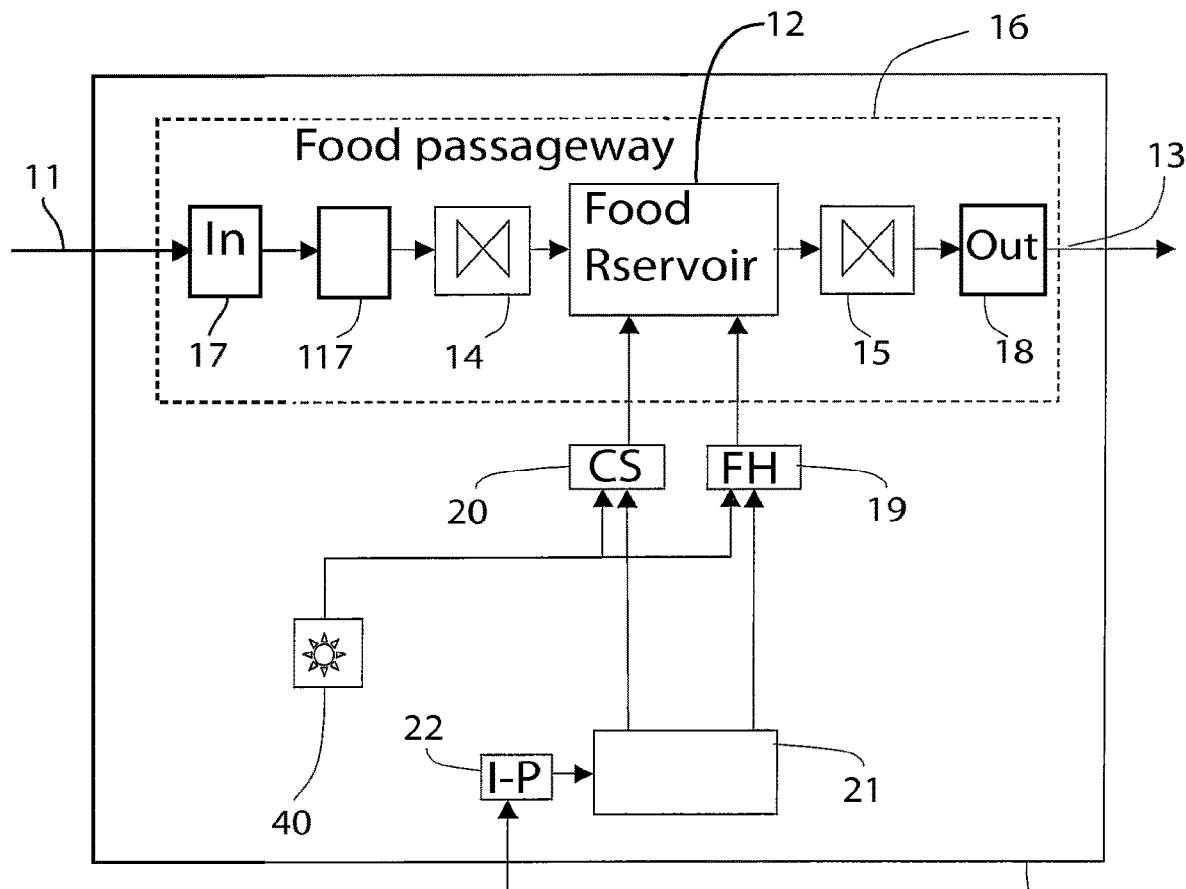
FIG. 4b is a block diagram illustrating an artificial stomach, in accordance with another embodiment.

Initially, food is allowed to enter into the food reservoir 12, optionally by opening the inlet valve 14 while maintaining the optional outlet valve 15 in a closed position (see FIG. 4b). This food may increase the volume of the food reservoir 12 and thereby compress the servo reservoir 90 so that part of the fluid contained therein is moved to the hydraulic fluid reservoir 52. The inlet valve is closed and fluid is moved repeatedly between the hydraulic fluid reservoir 52 and the servo reservoir 90. When fluid is moved into the servo reservoir 90, the inner wall 552 presses against the food contained in the food reservoir 12, thereby treating it in a way similar to that of the walls of a natural stomach. Furthermore, by releasing various chemicals a chemical treatment is achieved, as described above.

Emptying the food reservoir 12 may be done in different ways depending on if the optional outlet valve 15 is arranged at the outlet end of the artificial stomach or not.

When the food contained in the food reservoir has been sufficiently treated, and if an outlet valve 15 is present, the outlet valve 15 is opened and the servo reservoir 90 is filled with fluid so that the food reservoir 12 is emptied or at least essentially emptied. The food reservoir is adapted to empty step by step, small portions at a time. The outlet valve 15 is then closed, fluid is moved from the servo reservoir 90 to the hydraulic fluid reservoir 52, and the process is repeated over again. The outlet valve may also be adapted to functioning passively and to open related to a volume decrease in the food reservoir.

The above mentioned moving of fluid from the servo reservoir 90 to the hydraulic fluid reservoir 52 is preferably done in one of two ways: either the food entering the food reservoir 12 from the inlet 11 presses on the flexible wall 552 of the servo reservoir 90 thus emptying fluid therefrom to the hydraulic fluid reservoir 52 via the return conduit 118; or the food sensor 117 sends signals to the pump 44 when food is to enter the food reservoir 12 the pump 44 thus pumping out to said food corresponding amount of fluid from the servo reservoir 90 to the hydraulic fluid reservoir 52 via conduits 44a, 44b. If the emptying of the servo reservoir 90 is done in one of the above ways, entry of already treated food from the intestine 210 into the food reservoir 12 is avoided.

When the food contained in the food reservoir has been sufficiently treated, and if no optional outlet valve 15 is present, the servo reservoir 90 is filled with fluid stepwise, i.e. step by step in small steps so that the food reservoir 12 is emptied or at least essentially emptied in small steps which results in that the sufficiently treated food is received by the intestine in small subsequent steps thereby making it possible for the intestine to treat it without difficulty, i.e. the food reservoir is adapted to empty step by step, small portions at a time. Thereafter, fluid is moved from the servo reservoir 90 to the hydraulic fluid reservoir 52, and the process is repeated over again.

The above mentioned moving of fluid from the servo reservoir 90 to the hydraulic fluid reservoir 52 is preferably done in one of two ways: either the food entering the food reservoir 12 from the inlet 11 presses on the flexible wall 552 of the servo reservoir 90 thus emptying fluid therefrom to the hydraulic fluid reservoir 52 via the return conduit 118; or the food sensor 117 sends signals to the pump 44 when food is to enter the food reservoir 12 the pump 44 thus pumping out to said food corresponding amount of fluid from the servo reservoir 90 to the hydraulic fluid reservoir 52 via conduits 44a, 44b. If the emptying of the servo reservoir 90 is done in one of the above ways, entry of already treated food from the intestine 210 into the food reservoir 12 is avoided.

As mentioned above, a return conduit 118 may be arranged between the fluid reservoir 52 and the servo reservoir 90 if the food reservoir of the artificial stomach is adapted to increase in volume when filled with food when the patient is eating, thereby causing a change in the volume of the servo reservoir, in turn moving fluid between said servo reservoir and said hydraulic fluid reservoir via said return conduit 118. Said return conduit 118 is preferably of smaller diameter than the conduits 44a, 44b.

Corresponding processed can be applied to the embodiments described above with reference to FIGS. 5 and 6.

Optionally, the pump 44 may be comprised in an operating unit (not shown), implanted subcutaneously under the patient's skin. The operating unit may also comprise various additional components as e.g. injection port, a special container, as described above, and/or a switch for controlling the artificial stomach 10 (not shown).

Optionally, a pumping reservoir may be provided, preferably subcutaneously, like in the embodiment described above with reference to FIGS. 30a-c.

Optionally, the inlet 11 and the outlet 13 of the food reservoir 12 may be provided with non return valves 14 and 15, respectively. Furthermore, in addition the food reservoir 12 may also be provided with a burp output 566, which may comprise a burp valve 568, which bypasses the inlet valve 14 to allow gases from the food reservoir 12 to leave through the oesophagus 202.

Figure 34:
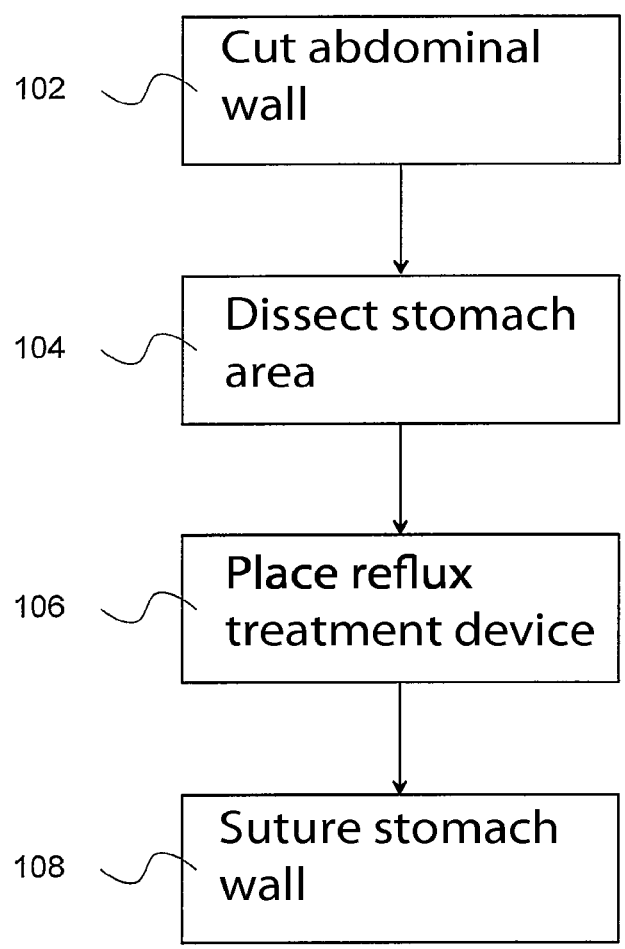
FIG. 34 is a flow chart describing a method of implanting an artificial stomach according to the invention into a human or animal patient.

In FIG. 34 a flow chart illustrating steps performed when implanting an artificial stomach in accordance with the present invention. First in a step 102, an opening is cut in the abdominal wall. Next, in a step 104 an area around the stomach is dissected. Thereupon, in a step 106 at least one artificial stomach in accordance with the invention is placed in contact with the stomach wall, in particular the fundus wall. The stomach wall is then sutured in a step 108. As can be seen from FIGS. 5, 6 and 33, in some embodiments of the invention an outer wall encloses both the food reservoir and a servo reservoir, the servo reservoir regulating the size of the food reservoir, the food reservoir and the servo reservoir being separated by a flexible inner wall, where further both the food reservoir wall and the servo reservoir wall comprise parts of the outer wall and the flexible inner wall. As can be seen from said FIGS. 5, 6 and 33, the servo reservoir may be a bellow, and the regulating means may be a gear or a fluid. The servo reservoir is adapted to have a variable size and to be filled with different amounts of fluid. The servo reservoir is adapted to have a shape allowing variation in size without limitation from surrounding fibrosis, covering the implant when implanted. The artificial stomach further comprises a hydraulic fluid reservoir, hydraulically connected to said servo reservoir and a pump for fluid connecting the fluid supply reservoir to the servo reservoir, wherein said pump for fluid connecting the hydraulic fluid reservoir to the servo reservoir is adapted to reversible move fluid between the servo reservoir and the hydraulic fluid reservoir.

In some embodiments, an outer wall encloses both the food reservoir and a servo reservoir for regulating the size of the food reservoir, the food reservoir and the servo reservoir being separated by a flexible inner wall, where further both the food reservoir wall and the wall of the servo reservoir comprise parts of the outer wall and the flexible inner wall, wherein said servo reservoir is adapted to be filled with fluid in small steps, wherein the food reservoir is adapted to be emptied by the servo reservoir in small steps, when said servo reservoir is filled with said fluid in small steps, thereby emptying food in small steps into the intestine, when said artificial stomach is implanted.

According to one embodiment, a method of using the artificial stomach by regulating the artificial stomach post-operatively to slowly empty food in the artificial stomach into the intestine or adapting the stomach to receive food by filling the servo reservoir with fluid step by step in small steps so that the food reservoir is emptied or at least essentially emptied in small steps which results in food is received by the intestine in small subsequent portions.

Figure 35:
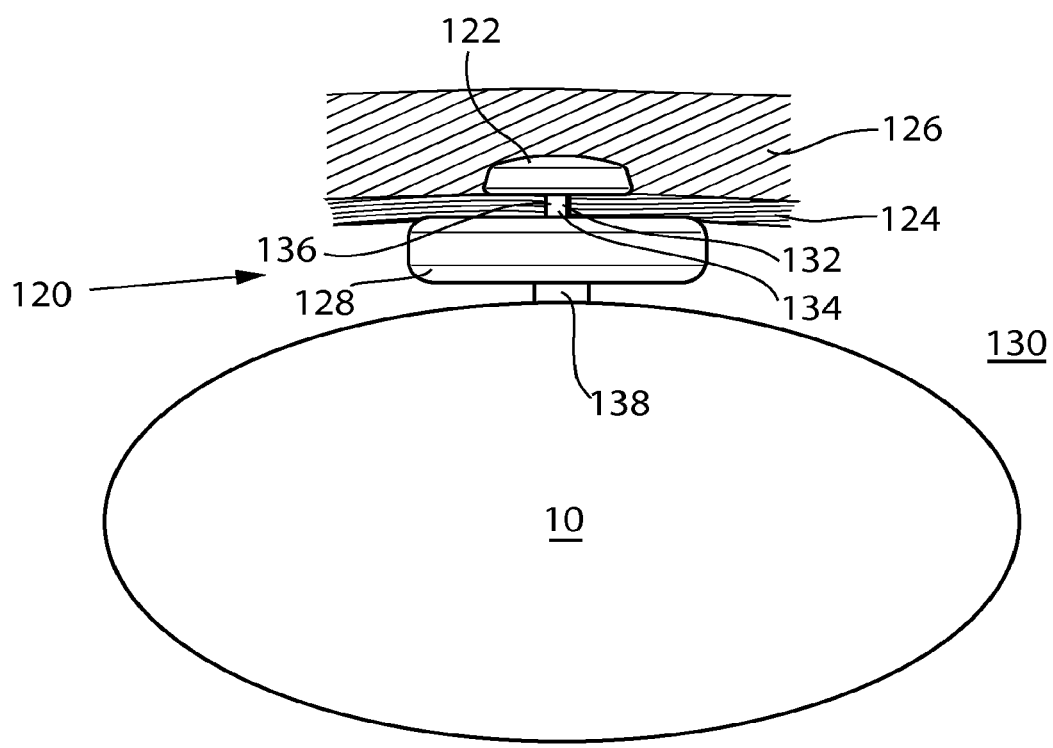
FIG. 35 is a side view of an embodiment of a fastening device for an artificial stomach according to the invention mounted to a body tissue.

FIG. 35 is a side view of an embodiment of a fastening device for an artificial stomach according to the invention mounted to a body tissue.

A fastening device for the artificial stomach may comprise a first unit adapted to be implanted at a first side of the abdominal wall in the patient, and where a second unit is adapted to be implanted in the abdominal cavity of the patient at a second side of the abdominal wall, and where the artificial stomach is fastened to the fastening device.

A fastening device 120 for the artificial stomach may be placed in the abdomen, thorax, muscle fascia (e.g. in the abdominal wall), preferably subcutaneously, or at any other suitable location.

The fastening device 120 comprises a first unit 122 preferably subcutaneously implanted at a first side of a body tissue 124 in the patient, such as the rectus abdominis muscle running vertically on each side of the anterior wall of the human abdomen. In other words, the first unit is positioned between the skin 126 of the patient and the body tissue 124.

A second unit 128 is implanted in a body cavity 130 of the patient at a second side of the body tissue 124, i.e., that the side opposite of the side at which the first unit 122 is provided.

The first and/or second units 122, 128 preferably have circular or elliptical cross-sectional shape when viewed from outside the patient's body. Combined with a smoothly curved sectional shape, this avoids any sharp corners on the units 122, 128, which could cause injuries to the patient in which the fastening device 120 is implanted.

The first and second units 122, 128 may be covered by a cover 132 made of for example silicone or another material providing protection. The cover 132, which preferably is resilient so as to follow the contours of the first and second units, also seals the fastening device 120 which also may be a control assembly, thereby protecting possible electronics and other sensitive components of the possible control assembly.

If a cover encloses the first and second units 122, 128, these will be kept together mechanically, thereby assisting an interconnecting device 134 in its interconnecting function.

The interconnecting device 134 constitutes a mechanical interconnection between the first and second units 122, 128 so that the fastening device 120 is kept in place by the body tissue 124. The interconnecting device has a cross-sectional area which is smaller than the cross-sectional area of the first unit and the second unit in a plane parallel to the extension of the body tissue. In this way, a hole 136 in the body tissue 124 through which the interconnecting device 134 extends can be sufficiently small so that it is avoided that one or the other of the units 122, 128 "slips through" the body tissue 124. Also, the cross-sectional shape of the interconnecting device 134 is preferably circular so as to avoid damage to the body tissue 124.

The interconnecting device 134 can be integral with one of the first and second units 122, 128. Alternatively, the interconnecting device 134 is a separate part, which is connected to the first and second units122, 128 during implantation of the fastening device 120.

In a preferred embodiment, the interconnecting device 134 is hollow so as to house various wires, hoses etc. electrically or hydraulically interconnecting the first and second units 122, 128 in case the fastening device 120 also is a control assembly.

Alternatively or additionally, the interconnecting device 134 is made of an elastic material, such as rubber, so that the fastening device 120 can adapt to the movements of the patient in which it is implanted.

The artificial stomach 10 is fastened to the fastening device 120 e.g. by using screws 138, rivets or the likeThe artificial stomach may comprise different material in layers, wherein at least one of said food reservoir, a servo reservoir for controlling the food reservoir and a hydraulic fluid reservoir for controlling the servo reservoir, of said artificial stomach may be provided with at least one layer. The at least one layer may comprise a Parylene layer, or a polytetrafluoroethylene layer, or a polyurethane layer, or a silicon layer, or a metal layer, or a Teflon® layer.

The metal layer may comprise any of gold, silver, and titanium, or a combination thereof.

The artificial stomach may be provided with a plurality of layers. The artificial stomach may comprise an outer surface layer of polyurethane, Teflon®, or polytetra-fluoroethylene, Parylene, silicone, metal, or a combination thereof.

The artificial stomach may comprise an inner surface layer of polyurethane, Teflon®, or polytetrafluoroethylene, Parylene, silicone, metal, or a combination thereof.

The artificial stomach may comprise an inner surface layer of polytetrafluoro-ethylene and an outer layer of silicone.

The artificial stomach may comprise an inner surface layer of polytetrafluoro-ethylene, an intermediate layer of silicone, and an outer layer of Parylene.

The artificial stomach may comprise an inner surface layer of polyurethane and an outer layer of silicone.

The artificial stomach may comprise an inner surface layer of polyurethane, an intermediate layer of silicone, and an outer layer of Parylene.

The artificial stomach may comprise an outer layer that includes a biocompatible material Please note that all the embodiments or features of an embodiment as well as any method or step of a method could be combined in any way if such combination is not clearly contradictory. Please also note that the description in general should be seen as describing both an apparatus or device adapted to perform a method as well as this method in itself.

While specific embodiments of the invention have been illustrated and described herein, it is realized that numerous other embodiments may be envisaged and that numerous additional advantages, modifications and changes will readily occur to those skilled in the art without departing from the spirit and scope of the invention. Therefore, the invention in its broader aspects is not limited to the specific details, representative devices and illustrated examples shown and described herein. Accordingly, various modifications may be made without departing from the spirit or scope of the general inventive concept as defined by the appended claims and their equivalents. It is therefore to be understood that the appended claims are intended to cover all such modifications and changes as fall within a true spirit and scope of the invention. Numerous other embodiments may be envisaged without departing from the spirit and scope of the invention.

The invention claimed is:

1. An artificial stomach for replacing the normal stomach of a patient comprising:
   a food reservoir adapted to collect food,
   an inlet connected to a first opening of the food reservoir and further being adapted to upstream connect to at least one of: the patient's esophagus and intestine, and
   an outlet connected to a second opening of the food reservoir and further being adapted to downstream connect to the patient's gastrointestinal tract,
   a servo reservoir for regulating the size of the food reservoir,
   wherein an outer wall encloses both the food reservoir and the servo reservoir the food reservoir and the servo reservoir being separated by an inner wall, and
   wherein both a wall of the food reservoir and a wall of the servo reservoir comprise parts of the outer wall and the inner wall.

2. The artificial stomach according to claim 1, wherein the servo reservoir is a bellow.

3. The artificial stomach according to claim 1, wherein emptying of the food reservoir is directly or indirectly regulated by a gear construction driven by a motor, and wherein the artificial stomach further comprises a servo system connected to the motor, to save force against longer strokes.

4. An artificial stomach for replacing the normal stomach of a patient comprising:
- a food reservoir adapted to collect food,
- an inlet connected to a first opening of the food reservoir and further being adapted to upstream connect to the patient's gastrointestinal tract,
- an outlet connected to a second opening of the food reservoir and further being adapted to downstream connect to the patient's gastrointestinal tract,
- a servo reservoir for regulating the size of the food reservoir,
- an outer wall enclosing both the food reservoir and the servo reservoir, the food reservoir and the servo reservoir being separated by an inner wall, both a wall of the food reservoir wall and a wall of the servo reservoir comprising parts of the outer wall and the inner wall,
- wherein emptying of the food reservoir is directly or indirectly regulated by a gear construction driven by a motor,
- wherein a drive shaft connected to a servo system connected to the motor directly or indirectly affects the emptying of the food reservoir, and
- wherein the drive shaft comprises two ends comprising a thread, spiral ridges turning in different directions at the two ends, further comprising a nut placed on the shaft at each end of the drive shaft, the food reservoir comprising two movable walls of said reservoir, wherein said nuts is adapted to be placed onto said moving walls, the motor adapted to change the volume of said food reservoir, when turning said drive shaft placed into said nuts, by moving said movable walls.

5. The artificial stomach according to claim 1, wherein the servo reservoir is adapted to have a variable size and to be filled with different amounts of fluid, and wherein the servo reservoir is further adapted to have a shape allowing variation in size without limitation from surrounded fibrosis, covering the implant when implanted.

6. The artificial stomach according to claim 5, further comprising a hydraulic fluid reservoir, hydraulically connected to said servo reservoir and a pump for fluid connecting the hydraulic fluid reservoir to the servo reservoir, wherein the food reservoir is adapted to increase in volume when filled with food when the patient is eating, thereby causing a reduction in the volume of the servo reservoir, in turn, moving fluid from the servo reservoir to the hydraulic fluid reservoir, and wherein the pump for fluid connecting the hydraulic fluid reservoir to the servo reservoir is adapted to move liquid from the hydraulic fluid reservoir to the servo reservoir or reversibly move fluid between the servo reservoir and the hydraulic fluid reservoir.

7. The artificial stomach according to claim 5, wherein said servo reservoir is adapted to be regulated by manually pressing a pumping reservoir in fluid connection with the servo reservoir.

8. The artificial stomach according to claim 1, wherein the outer wall is substantially rigid, the stomach food part comprises the food reservoir and the servo reservoir, the hydraulic fluid reservoir is separated from the stomach food part by the rigid outer wall and is further enclosed by a fluid reservoir wall, and the artificial stomach is adapted to he implanted in the patient's abdomen.

9. The artificial stomach according to claim 8, wherein said food reservoir is adapted to increase in volume when filled with food when the patient is eating, thereby causing a reduction in the volume of the servo reservoir, in turn moving fluid from said servo reservoir to said hydraulic fluid reservoir.

10. The artificial stomach according to claim 1, wherein the outlet is further adapted to downstream connect to the intestine, the artificial stomach further comprising:
- an inlet valve adapted to be connected between the patient's gastrointestinal tract and the inlet connected to the first opening of the food reservoir, wherein at least one of:
- the inlet valve is adapted to open correlated to when food in the gastrointestinal tract upstream is transported down,
- the inlet valve is adapted to open correlated to when a contracting wave is propagating along the gastrointestinal tract upstream, and
- the inlet valve is adapted to open correlated to when food is reaching the inlet valve, and
- an outlet valve connected between the second opening of the food reservoir and the outlet, wherein at least one of:
- the outlet valve is adapted to open when the food reservoir should be emptied,
- the outlet valve is adapted to open at a regulated rate, the food reservoir is adapted to empty open step by step, small portions at a time, and
- the outlet valve is adapted to functioning passively and opens related to a volume decrease in the food reservoir.

11. The artificial stomach according to claim 1, wherein the artificial stomach further comprises an inlet valve unit comprising an inlet valve and a burp output, and wherein the burp output further comprises a burp valve connecting the food reservoir with the inlet valve proximal to said burp valve.

12. The artificial stomach according to claim 1 further comprising at least one connector, the at least one connector being adapted to upstream connect the inlet to the patient's gastrointestinal tract, and/or downstream connect the outlet to the patient's gastrointestinal tract, wherein the connector comprises at least one of:
- a conduit fixedly attached at a first, proximal end on the outside the artificial stomach and in fluid connection to the food passageway, where a proximal part of the conduit is formed like a tube, and distal to the tube a bulge is formed, and a blocking ring arranged to be pushed against the bulge, the ring having an inner diameter less than the outer diameter of the bulge but large enough to allow an intestinal/oesophageal wall to be placed between the ring and the tube, so as to thereby be adapted to stop the intestinal/oesophageal wall from slipping away from the tube,
- wherein the blocking ring is arranged to be pushed over a flexible sleeve or the intestine against the bulge, thereby being adapted to stop the intestinal/oesophageal wall from slipping away from the tube, and
- a sleeve adapted to cover a part of a wall of the gastrointestinal tract, wherein the sleeve has a structure adapted to promote in-growth of human tissue into the sleeve, wherein the flexible sleeve is arranged to at least one of: cover a part of the wall of the gastrointestinal tract, and to be rolled upon itself and then unrolled to cover part of the tube and the oesophagus or intestine, which is arranged to be pulled over the second end of the conduit sufficiently far so as to extend also over the bulge.

13. The artificial stomach according to claim 1, further comprising at least one of a food handling system and a cleaning system,
- the food handling being adapted to at least one of:

mechanically handle food in the food reservoir,
move the food around in the food reservoir,
cut food in the food reservoir using electrically driven rotating knifes,
squeeze food in the food reservoir,
chemically handle food in the food reservoir, and
release at least one liquid in the food reservoir, the liquid being adapted to treat the food in the food reservoir, and
the cleaning system being adapted to clean the surface of the food reservoir by releasing at least one liquid into the food reservoir.

14. The artificial stomach according to claim 13, further comprising a special container,
wherein the special container is adapted to accumulate and distribute at least one of: liquid to the food handling system, and liquid to the cleaning system, and
wherein the liquid to the food handling system comprises at least one of: an acid, an enzyme, and an anti-bacterial substance,
wherein the liquid to the cleaning system comprises at least one of: a cleaning substance, and an anti-bacterial substance,
and wherein the artificial stomach further comprises at least one injection port adapted to be placed subcutaneously in the patient and connected to the artificial stomach and adapted to be injected with at least one liquid selected from a set of: a liquid comprising an anti-bacterial substance, an acid, a liquid comprising a cleaning substance, and a liquid visible on x-ray.

15. The artificial stomach according to claim 6, wherein at least one of said food reservoir, a servo reservoir for controlling the food reservoir and a hydraulic fluid supply reservoir for controlling the servo reservoir, of said artificial stomach is provided with at least one layer that is an inner layer or an outer layer comprising at least one:
a Parylene layer,
a polytetrafluoroethylene layer,
a polyurethane layer,
a silicon layer,
a metal layer, and
a metal layer comprising at least one of: gold, silver, and titanium, or a combination thereof.

16. The artificial stomach according to claim 1, wherein moving of fluid from the servo reservoir to the hydraulic fluid reservoir is done by that at least one of:
food entering the food reservoir from the inlet pressing on the flexible wall of the servo reservoir, thus emptying fluid from the servo reservoir to the hydraulic fluid reservoir via a return conduit, wherein the return conduit is arranged between the hydraulic fluid reservoir and the servo reservoir for moving fluid between the servo reservoir and the hydraulic fluid reservoir via the return conduit, and
a food sensor sending signals to the pump when food enters the food reservoir, the pump pumping out to the food a corresponding amount of fluid from the servo reservoir to the hydraulic fluid reservoir.

17. The artificial stomach according to claim 1 being adapted to regulate the artificial stomach postoperatively to slowly, step by step, empty food in the artificial stomach into the intestine, and being adapted to fill the servo reservoir with fluid, step by step, in small steps so that the food reservoir is emptied or at least essentially emptied in small steps which results in food being received by the intestine in small subsequent portions.

18. The artificial stomach according to claim 1 further comprising a fastening device for the artificial stomach, adapted to at least one of:
be fastening the artificial stomach,
be fastened by using screws, rivets or another kind of fastener,
be made of elastic material to adapt to movements of the patient,
be divided in first and second units,
be interconnected between divided first and second units of the fastening device by an interconnecting device,
be placed in the abdomen,
be placed in the thorax,
be placed subcutaneously,
be placed in the abdominal wall, and
be placed by a muscle fascia.

19. The artificial stomach according to claim 1 further comprising an operation device for operating the artificial stomach, wherein the operation device comprises at least one of:
a motor,
a pump,
an electrically operated operation device,
an electric motor, and
a hydraulic operation device, and
wherein the artificial stomach further comprises at least one of:
an internal energy source comprising a battery to power the operation device,
an internal energy source comprising an accumulator to power the operation device,
a remote control,
a receiver for receiving signals from a remote control, and
a subcutaneous switch for non-invasively regulating a function of the artificial stomach.

20. A system including the artificial stomach according to claim 1, comprising an energy source adapted to power the artificial stomach, wherein the energy source comprises at least one of:
an internal energy source,
an internal energy source adapted to be charged by energy in a wireless mode to receive energy from an external energy source transmitting energy in a wireless mode,
a wireless energy transmitter adapted to non-invasively energize the internal energy source,
a wireless energy transmitter adapted to non-invasively energize the artificial stomach,
an energy-transforming device to transform wireless energy from a first form into a second form energy,
an energy-transforming device for transforming wireless energy from a first form into a second form energy, adapted to directly during energy transfer operate the artificial stomach with a second form energy, and
wirelessly transmitted energy, first form energy, to directly in its wireless form affect the operation device to create kinetic energy to adjust the device during energy transfer.

21. The system according to claim 20, comprising a sensor arranged to sense a functional parameter of the artificial stomach or a physical parameter of the patient.

22. The system according to claim 21, comprising a feed back device and an internal control unit, wherein the internal control unit is acting in response to the physical parameter or functional parameter sensed by the sensor to control the artificial stomach, wherein the sensor is arranged to register at least one of:

parameters relating to the powering of the artificial stomach or the system,
when food is arriving to the artificial stomach, and
that food is arriving to the artificial stomach by registering a change in volume of the oesophagus or a change of the curvature or elongation of the oesophagus wall, when the sensor is arranged on or at the oesophagus wall.

* * * * *